(12) United States Patent
Nakamura et al.

(10) Patent No.: US 7,563,768 B2
(45) Date of Patent: Jul. 21, 2009

(54) ASTHMA PREPARATION

(75) Inventors: Toshikazu Nakamura, 1-4, Hoshojicho, Okazaki, Sakyo-ku, Kyoto-shi, Kyoto 606-8333 (JP); Arihiko Kanehiro, Okayama (JP); Mitsune Tanimoto, Okayama (JP); Wataru Ito, Okayama (JP); Kunio Matsumoto, Mino (JP)

(73) Assignees: Kringle Pharma Inc., Osaka (JP); Toshikazu Nakamura, Kyoto (JP)

( * ) Notice: Subject to any disclaimer, the term of this patent is extended or adjusted under 35 U.S.C. 154(b) by 150 days.

(21) Appl. No.: 10/550,505

(22) PCT Filed: Mar. 24, 2004

(86) PCT No.: PCT/JP2004/004133

§ 371 (c)(1),
(2), (4) Date: Aug. 23, 2006

(87) PCT Pub. No.: WO2004/084934

PCT Pub. Date: Oct. 7, 2004

(65) Prior Publication Data

US 2007/0213261 A1    Sep. 13, 2007

(30) Foreign Application Priority Data

Mar. 26, 2003  (JP) ............................. 2003-086268

(51) Int. Cl.
*A61K 38/18* (2006.01)

(52) U.S. Cl. ...................................................... 514/12
(58) Field of Classification Search ................... None
See application file for complete search history.

(56) References Cited

U.S. PATENT DOCUMENTS 5,855,918 A    1/1999   Mrsny et al.
7,074,764 B2 *  7/2006  Schwartz ..................... 514/12

FOREIGN PATENT DOCUMENTS

| JP | 11-512435 | 10/1999 |
| JP | 2000-239182 | 9/2000 |
| WO | 97/09997 | 3/1997 |

OTHER PUBLICATIONS

Ito et al., International Archives of Allergy and Immunology, 145:324-339, 2008.*
Ito et al., American Journal of Respiratory Cell and Molecular Biology, 32:268-280, 2005.*
Funakoshi et al., Clinica Chimica Acta, 327(1-2):1-23, Jan. 2003.*
W. D. Kim, "Lung Mucus: A Clinician's View", European Respiratory Journal, vol. 10, pp. 1914-1917, 1997.

* cited by examiner

*Primary Examiner*—Marianne P Allen
(74) *Attorney, Agent, or Firm*—Wenderoth, Lind & Ponack, L.L.P.

(57) ABSTRACT

A preventive or therapeutic agent for asthma, comprising HGF or its salt as an active ingredient.

10 Claims, 9 Drawing Sheets (a)

(b)

(c)

(a)

(b)

(c)

ated to ovalbumin-sensitized mice exposed to antigen inhalation, invasion of inflammation cells such as eosinophils and lymphocytes seen at the time of inflammation is suppressed, and increase in a concentration of Th2 cytokines such as IL-4, IL-5 and IL-13, and growth factors such as platelet-derived growth factor (PDGF) and nerve growth factor (NGF) in a bronchoalveolar lavage fluid is remarkably suppressed, and it
ASTHMA PREPARATION This application is a U.S. national stage of International Application No. PCT/JP2004/004133 filed Mar. 24, 2004.

1. Technical Field

The present invention relates to an asthma preparation. More particularly, the present invention relates to a safe preventive or therapeutic agent for asthma, which extremely effectively suppresses an inflammation reaction in bronchial asthma, and has no side effects.

2. Background Art

In the modern society, atmospheric pollution has become remarkably increased due to exhaust gases, chemical substances or dusts from automobiles or factories, and accompanying this, the number of patients with bronchial asthma has been increased.

Bronchial asthma is a severe disease in which constriction and contraction of the bronchial smooth muscle occur at the time of the seizure, and at the time of status asthmatics, a patient is lead to suffocation death from the state of very painful dyspnea. Bronchial asthma is the most frequent cause for hospitalization not only in adults but also in children and, by present medical care, bronchial asthma is thought to be a disease for which prevention and treatment corresponding to asthma in individual patients are difficult.

It is generally thought that bronchial asthma is developed due to a causal factor or a contribution factor such as antigen stimulation (e.g. house dust mite, pet, pollen, the aforementioned exhaust gas, chemical substance, dust, etc.) in addition to constitutional cause such as airway hypersensitivity to a chemical transmitter and other factors. The pathophysiology is complicated, many researchers show the facts that a variety of factors such as invasion of inflammatory cells such as activated eosinophils and T lymphocytes into the bronchial mucosa and, thereupon, Th2 cytokines, particularly interleukin-4 (IL-4), interleukin-5 (IL-5), interleukin-13 (IL-13), and growth factors such as platelet-derived growth factor (PDGF), nerve growth factor (NGF), and transforming growth factor (TGF-β), inter alia, particularly TGF-β, play an important role in accelerating a series of inflammation reactions, however, a full view of the mechanism has not been elucidated yet.

When inflammation is developed frequently, and furthermore incomplete treatment is continued for a long term, for example, fibrosis of subepithelial tissue, and excessive growth of goblet cells and myofibroblasts occur and, as a result, bronchia is regenerated in a form of incomplete repair (remodeling). Once incomplete repair occurs, the bronchial mucosa is replaced with a fibrous tissue and its elasticity is lost, and thus reversibility of the respiration tract is lost, leading to chronic or refractory asthma.

Currently, for treating such chronic bronchial asthma, adrecocortical hormones, a so-called steroidal agent is mainly used. However, this drug is effective in the treatment, but it causes problematic side effects. For example, glucocorticosteroids which are known as an effective anti-asthma drug actually has only transient abating effect to the symptom and, as a sacrifice, the well-known side effects such as osteoporosis, obesity, hypertension and diabetes are accompanied (e.g. see Barnes, P. J., "A new approach to the treatment of asthma", USA, N Engl J Med, Massachusetts Medical Society, 321, p1517-1527 (1989)). Inhalation steroid therapy which has been developed in order to alleviate side effects due to the steroid has a risk of developing complication (e.g. see Toogood, J. H., "Influence of dosing frequency and schedule on the response of chronic asthmatics to the aerosol steroid, budesonide", Journal of Allergy and Clinical Immunology, USA, 70, p388-398 (1982)). In particular, for patients suffering from a severe side effect due to a steroid, a low-dose methotrexate has been proposed as a substitute for steroids (e.g. see Mullarkey, M. F., "Methotrexate in the treatment of corticosteroid-dependent asthma. A double-blind crossover study", N. Engl. J. Med., USA, Massachusetts Medical Society, 318, p603-607 (1988)), but methotrexate itself has considerable toxicity.

In addition, there is a rapid-acting drug which dilates a bronchia such as a β2 stimulating agent, but since the drug also acts on a heart, this can not be used in patients having a cardiac disease, and the frequency of its use is restricted.

Therefore, any of the current anti-asthma agents or asthma therapy is incomplete in the effect and safety, and long acting remission has not been reported yet. Therefore, therapeutic agents and methods for bronchial asthma which are not harmful to patients and exert long-acting antiinflammatory effect are demanded.

Hepatocyte growth factor (HGF) refers to a heterodimer protein composed of an α chain and a β chain consisting of an N-terminal hairpin domain and four kringle domains. HGF is known to be an important factor responsible for mediating epithelial-mesenchymal interaction in a variety of epithelial cell systems. For example, HGF is known to have mitogenic activity of inducing invasion and metastasis of tumor cells, motogenic activity, morphogenic activity and angiogenesis activity (e.g. see Nakamura T., "Purification and subunit structure of hepatocyte growth factor from rat platelets", FEBS letters, USA, 224, p311-316 (1987), Jiang. W. G et al., Crit. Rev. Oncol. Hematol., 29, p209-248 (1999)). In addition, it is also known that, by administering HGF to a human, etc., development of fibrosis of liver, kidney, lung or cardiac muscle (e.g. cirrhosis in liver) can be prevented, and progression of such fibrosis can be arrested (e.g. see Ueki K. et al., "Hepatocyte growth factor gene therapy of liver cirrhosis in rats", Nature Medicine, 5, p226-230 (1999)).

Although HGF has a variety of biological activities as described above, it has not been known at all that HGF also has the effect of suppressing airway inflammation due to asthma, and this has been elucidated for the first time by the present invention.

Accordingly, the present invention is important in that the suppressing effect of HGF on airway inflammation was discovered. Moreover, it can be said that the therapeutic agent for asthma of the present invention is very excellent for the reasons that it is safer to a living body than the aforementioned steroid agent since the constitutional ingredient thereof is HGF derived from a living body, and also it causes no risk of development of side effects when administered.

DISCLOSURE OF THE INVENTION

An object of the present invention is to provide a therapeutic agent for asthma, more particularly, a therapeutic agent for asthma which contains HGF extremely effectively suppressing an inflammation reaction in bronchial asthma, has no side effects due to administration, and is safe to a living body.

In order to solve the aforementioned problems, the present inventors have continued to intensively study. Specifically, the present inventors have found that when HGF is administered to ovalbumin-sensitized mice exposed to antigen inhalation, invasion of inflammation cells such as eosinophils and lymphocytes seen at the time of inflammation is suppressed, and increase in a concentration of Th2 cytokines such as IL-4, IL-5 and IL-13, and growth factors such as platelet-derived growth factor (PDGF) and nerve growth factor (NGF) in a bronchoalveolar lavage fluid is remarkably suppressed, and it is useful to use HGF for treating or preventing airway inflammation such as asthma. The present inventors continued to further study based on these findings, which resulted in completion of the present invention.

That is, the present invention relates to:

(1) a preventive or therapeutic agent for asthma, comprising HGF or a salt thereof as an active ingredient, (2) the preventive or therapeutic agent for asthma according to (1), wherein HGF a peptide comprising an amino acid sequence represented by SEQ ID NO: 1 or 2, a peptide comprising an amino acid sequence substantially identical to an amino acid sequence represented by SEQ ID NO: 1 or 2, or a partial peptide thereof, (3) a preventive or therapeutic agent for asthma, comprising a DNA encoding HGF as an active ingredient, (4) the preventive or therapeutic agent for asthma according to (3), wherein the DNA encoding HGF is a DNA comprising a base sequence represented by SEQ ID NO: 3 or 4, or a base sequence which hybridizes with a base sequence represented by SEQ ID NO: 3 or 4 under highly stringent conditions, (5) the preventive or therapeutic agent for asthma according to (3) or (4), wherein the DNA encoding HGF is inserted into a recombinant expression vector, (6) the preventive or therapeutic agent for asthma according to (5), wherein the recombinant expression vector is adeno-associated virus (AAV), adenovirus, retrovirus, poxvirus, herpesvirus, herpes simplex virus, lentivirus (HIV), sendaivirus, Epstein-Barr virus (EBV), vaccinia virus, poliovirus, sindbis virus, SV40, pCAGGS, pBK-CMV, pcDNA3.1 or pZeoSV, (7) the preventive or therapeutic agent for asthma according to (5) or (6), wherein the recombinant expression vector is further contained in a host cell, (8) the preventive or therapeutic agent for asthma according to any one of (3) to (7), wherein the DNA encoding HGF, or the recombinant expression vector containing the DNA encoding HGF is contained in a liposome or a microcapsule, (9) the preventive or therapeutic agent for asthma according to any one of (1) to (8), further comprising a pharmaceutically acceptable carrier,

(10) a method for preventing or treating asthma, comprising suppressing airway inflammation by administering an effective amount of HGF or a salt thereof to a mammal,

(11) a method for preventing or treating asthma, comprising suppressing airway inflammation by administering an effective amount of a DNA encoding HGF to a mammal,

(12) use of HGF or a salt thereof for preparing a preventive or therapeutic agent for asthma, which comprises suppressing airway inflammation, and

(13) use of a DNA encoding HGF for preparing a preventive or therapeutic agent for asthma, which comprises suppressing airway inflammation.

BEST MODE FOR CARRYING OUT THE INVENTION

Figure 1:
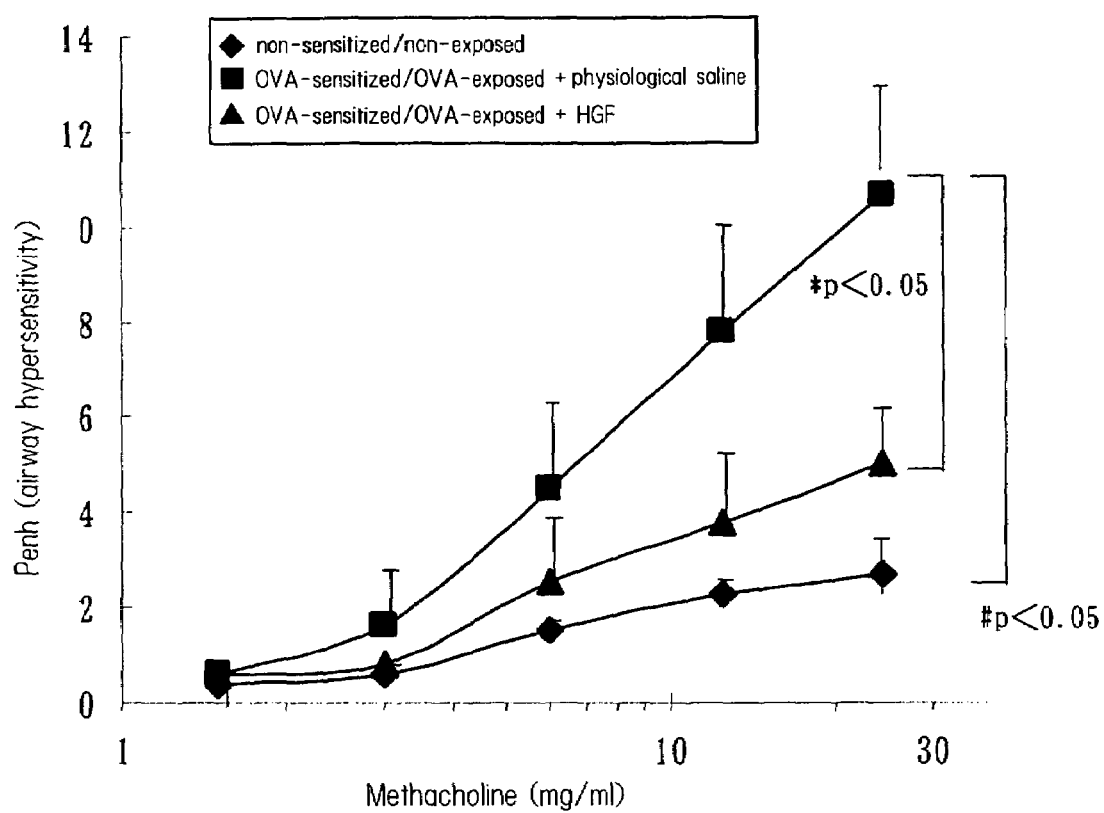
FIG. 1 is a view showing influence of HGF administration on airway hypersensitivity exasperation due to methacholine inhalation in a mouse model of bronchial asthma.

The present invention is characterized in that HGF or a salt thereof is contained as an active ingredient.

HGF or a salt thereof may be derived from a mammal, for example, any one of human, guinea pig, mouse, chicken, rabbit, pig, sheep, cow, and monkey. In addition, HGF may be a purified protein which is extracted from a tissue or a cell of the mammal, such as mature hepatocytes and platelets, or a recombinant protein obtained by culturing a transformed cell in which a DNA or an RNA encoding HGF has been introduced and purifying a produced protein using gene recombination technique, or a synthetic polypeptide which is chemically synthesized. Extraction and purification of HGF from mature hepatocytes or transformed cells, and preparation of synthetic polypeptides may be performed according to the method known per se.

Examples of a method of isolating or purifying HGF from a cell of a mammal such as human include a method of treating rat platelet containing HGF at a relatively high concentration with thrombin, obtaining HGF secreted outside the platelet, and purifying this using ion exchange chromatography, affinity chromatography with heparin Sepharose, or reversed-phase high performance liquid chromatography.

In addition, when HGF is obtained by culturing a transformed cell in which a DNA or an RNA encoding HGF has been introduced and purifying a secreted protein using gene recombination technique, this procedure may be performed according to the following method.

A DNA or an RNA encoding HGF is inserted into a suitable recombination expression vector such as pCAGGS [Gene, 108, 193-200 (1991)], and this is introduced into a host cell to construct a transformant.

As a method of introducing a recombinant expression vector into a host, any method may be used as far as it is the method known per se. Examples of such methods include a competent cell method [J. Mol. Biol., 53, 154(1970)], a DEAE dextran method [Science, 215, 166, (1982)], an in vitro packaging method [Proc. Natl. Acad. Sci., USA, 72, 581 (1975)], a virus vector method [Cell, 37, 1053 (1984)], a microinjection method [Exp. Cell. Res., 153, 347 (1984)], an electroporation method [Cytotechnology, 3, 133 (1990)], a calcium phosphate method [Science, 221, 551 (1983)], a lipofection method [Proc. Natl. Acad. Sci., USA, 84, 7413 (1987)], and a protoplast method [Japanese Patent Application Laid-Open (JP-A No. 63-2483942, Gene, 17, 107 (1982), Molecular & General Genetics, 168, 111 (1979)].

Examples of a host include bacteria, yeast, filamentous fungi, plant cells, and mammal cells. Examples of bacteria include *Escherichia, Enterobacter, Proteus, Salmonella, Serratia, Bacillus, Lactobacillus, Bifidobacterium, Pseudomonas, Streptomyces, Streptococcus, Leuconostoc*, and *Pediococcus*.

Examples of yeast include *Saccharomyces cerevisiae, Schizosaccharomyces pombe*, NCYC1913, NCYC2036, *Pichia pastoris*, and baker's yeast. Examples of filamentous fungi include *Aspergillus*, and *Penicillium*.

Examples of plant cells include cotton, corn, potato, *Vicia faba*, petunia, tomato, and tobacco. Examples of mammal cells include mouse C127 cells, Chinese hamster CHO cells, monkey COS cells, mouse BALB/3T3 cells, mouse L cells, mouse AtT-20 cells, mouse myeloma cells, rat GH3 cells, human HeLa cells, human FL cells, and 293 cells derived from human fetal kidney [Experimental medicine, 12, 316 (1994)].

For producing HGF, the resulting transformant is cultured in an adequate medium depending on a host. The medium contains a carbon source, an inorganic substance, a vitamin, serum and a drug necessary for the growth of the transformant.

When a host of a transformant is *Escherichia coli*, examples of the medium include an LB medium (Nissui Pharmaceutical Co., Ltd.), and an M9 medium [J. Exp. Mol. Genet., Cold Spring Laboratory, New York, 431(1972)]. When a host is yeast, examples of the medium include a YEPD medium [Genetic Engineering, vol. 1, Plenum Press, New York, 117 (1979)]. When a host is an animal cell, examples of the medium include a MEM medium containing 20% or less of bovine fetal serum, a DMEM medium, and a PRMI1640 medium (Nissui Seiyaku), though they are not limited thereto. A transformant is cultured usually at 20° C. to 45° C. within a pH range of 5 to 8, and if necessary, aeration/stirring is performed, though they are not limited thereto. When a host is an adhesive animal cell, a carrier such as glass beads, collagen beads, and acetylcellulose hollow fiber is used, if desired.

Since a transformant producing HGF secretes HGF in a supernatant of the culture solution, extraction of HGF may be performed using the transformant culture supernatant. Alternatively, it may be possible to extract HGF produced in the transformant. In order to extract a protein from cultured bacteria or cells, there is appropriately used a method of, after culturing, collecting bacteria or cells by the known method, suspending the bacteria or cells in a suitable buffer, destructing them by sonication, lysozyme or/and freezing/thawing, and obtaining a crude extract of HGF by centrifugation or filtration. A buffer may contain a protein denaturing agent such as urea and guanidine hydrochloride, or a surfactant such as Triton X-100™. Purification of HGF contained in the thus obtained culture supernatant or cell extract can be performed by appropriate combination of the separation/purification methods known per se. As such known separation/purification method, there are used a method of utilizing a solubility such as salting out and a solvent precipitation method; a method of mainly utilizing a difference in a molecular weight such as a dialysis method, an ultrafiltration method, a gel filtration method and a SDS-polyacrylamide gel electrophoresis method; a method of utilizing a charge difference, such as ion exchange chromatography; a method of utilizing specific affinity such as affinity chromatography; a method of utilizing a hydrophobicity difference, such as reversed-phase high performance liquid chromatography; and a method of utilizing an isoelectric point difference, such as an isoelectric focusing method.

An amino acid sequence represented by SEQ ID NO: 1 or 2 is an example of an amino acid sequence of HGF. An amino acid sequence represented by SEQ ID NO: 2 is an amino acid sequence in which $161^{st}$ to $165^{th}$ five amino acid residues of the amino acid sequence represented by SEQ ID NO: 1 are deleted, but both of proteins having an amino acid sequence represented by SEQ ID NO: 1 or 2 are human-derived natural HGF, and have mitogenic and motogenic activities of HGF.

As a peptide comprising an amino acid sequence substantially identical to the amino acid sequence represented by SEQ ID NO: 1 or 2, there is preferably exemplified a peptide comprising an amino acid sequence having at least 70% or more, preferably about 80%, further preferably about 90% or more, most preferably about 95% or more identity with the amino acid sequence represented by SEQ ID NO: 1 or 2, such as a peptide comprising an amino acid sequence in which one to several amino acid residues are inserted to or deleted from the amino acid sequence represented by SEQ ID NO: 1 or 2, an amino acid sequence in which one to several amino acid residues are substituted with other amino acid residues, or an amino acid sequence in which one to several amino acid residues are modified, and having airway inflammation suppressing activity at asthma attack. An amino acid to be inserted, or an amino acid to be substituted may be a non-natural amino acid other than 20 kinds of amino acids encoded by a gene.

These peptides may be alone, or a peptide comprising an amino acid sequence of a combination of insertion, deletion and substitution, or a mixed peptide thereof.

HGF used in the present invention may have a C-terminus of any one of carboxyl group (—COOH), carboxylate (—COO⁻), amide (—CONH$_2$) and ester (—COOR). Herein, as R in ester, a $C_{1-6}$ alkyl group such as methyl, ethyl, n-propyl, isopropyl and n-butyl, a $C_{3-8}$ cycloalkyl group such as cyclopentyl and cyclohexyl, a $C_{6-12}$ aryl group such as phenyl and α-naphthyl, and a $C_{7-14}$ aralkyl group such as a phenyl-$C_{1-2}$alkyl group such as benzyl and phenethyl, and an α-naphthyl-$C_{1-2}$ alkyl group such as α-naphthylmethyl, as well as a pivaloyloxymethyl group which is generally used as an oral ester are employed. When HGF used in the present invention has a carboxyl group (or carboxylate) at a position other than the C-terminus, HGF in which a carboxyl group is amidated or esterified is also included in HGF of the present invention. In this case, as an ester, for example, the aforementioned ester at the C-terminus is used. Further, HGF used in the present invention includes the aforementioned protein in which an amino group of a methionine residue at the N-terminus is protected with a protecting group (a $C_{1-6}$ acyl group such as a $C_{2-6}$ alkanoyl group such as formyl and acetyl), or a glutamyl group produced by cleavage of the N-terminal side in a living body is converted into pyroglutamic acid, or a substituent (e.g. —OH, —SH, amino group, imidazole group, indole group, guanidino group, etc.) on a side chain of amino acids in the molecule is protected with a suitable protecting group (e.g. a $C_{1-6}$ acyl group such as a $C_{2-6}$ alkanoyl group such as formyl and acetyl), or a conjugated protein such as a so-called glycoprotein to which a sugar chain is bound.

As a partial peptide of HGF used in the present invention (hereinafter, abbreviated as partial peptide in some cases), any peptide may be used as far as it is a partial peptide of the aforementioned HGF. In the present invention, with respect to the number of amino acids of a partial peptide, there is preferably exemplified a peptide comprising an amino acid sequence of at least about 20 or more, preferably about 50 or more, more preferably about 100 or more among the amino acid sequence constituting the aforementioned HGF. In the partial peptide of the present invention, the C-terminus may be any one of carboxyl group (—COOH), carboxylate (—COO⁻), amide (—CONH$_2$) and ester (—COOR). Further, as in the aforementioned HGF, the partial peptide includes a peptide in which the amino group of a methionine residue at the N-terminus is protected with a protecting group, a peptide in which Gln produced by cleavage of the N-terminal side in a living body is converted into pyroglutamic acid, a peptide in which a substituent on a side chain of an amino acid in the molecule is protected with a suitable protecting group, or a composite peptide such as a so-called glycopeptide to which a sugar chain is bound.

Examples of a salt of HGF or a partial peptide used in the present invention include physiologically acceptable salts with acids or bases, and inter alia, physiologically acceptable acid addition salts are preferable. Examples of such salt include salts with inorganic acids (e.g. hydrochloric acid, phosphoric acid, hydrobromic acid, sulfuric acid), and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

A partial peptide of HGF or a salt thereof used in the present invention can be prepared according to the known peptide synthesis procedures, or through cleavage of HGF with a suitable peptidase. As the peptide synthesis procedures, for example, any one of a solid phase synthesis and a liquid phase synthesis may be used. That is, an objective peptide can be prepared by condensing an HGF-constituting partial peptide or amino acids with a remaining part, followed by removal of the protecting group if the product has a protecting group. Examples of the known condensation method and protecting group removal includes the methods described, for example, in M. Bodanszky and M. A. Ondetti, Peptide Synthesis, Interscience Publishers, New York (1966), and Schroeder and Luebke, The peptide, Academic Press, New York (1965).

In addition, after the reaction, a partial peptide of HGF can be purified and isolated by combination of the conventional purifying methods such as solvent extraction, distillation, column chromatography, liquid chromatography, and recrystallization. When a partial peptide obtained by the aforementioned method is a free form, it can be converted into a suitable salt by the known method. Conversely, when a partial peptide is obtained as a salt, it can be converted into a free form by the known method.

The present invention may contain a DNA encoding HGF as an active ingredient.

As a DNA encoding HGF used in the present invention, any one of a genome DNA, a genome DNA library, a cDNA derived from the aforementioned cell or tissue, a cDNA library derived from the aforementioned cell or tissue, and a synthetic DNA may be used. A vector used in the library may be any one of bacteriophages, plasmids, cosmids, and phagemides. Alternatively, a DNA may be obtained by preparing a total RNA or a mRNA fraction from the aforementioned cell or tissue, followed by amplification using a direct RT-PCR method. Specifically, examples of a DNA encoding HGF include (a) a DNA having a base sequence represented by SEQ ID NO: 3 or 4, and (b) a DNA which hybridizes with a DNA having a base sequence represented by SEQ ID NO: 3 or 4 under stringent conditions, said DNA encoding a protein having substantially the same quality of activity as that of HGF, such as mitogenic activity, and motogenic activity. In addition, a DNA which hybridizes with a DNA having a base sequence represented by SEQ ID NO: 3 or 4 means a DNA obtained, for example, by using the aforementioned DNA as a probe employing a colony hybridization method, a plaque hybridization method or a Southern blot hybridization method. Specifically, examples of such DNAs include a DNA which can be identified by performing hybridization at about 65° C. in the presence of about 0.7 to 1.0 M sodium chloride using a filter on which a DNA derived from a colony or a plaque is immobilized, and then washing the filter under the condition of about 65° C. using a SSC solution having a concentration of about 0.1 to 2-fold (1-fold concentration of SSC solution has a composition of 150 mM sodium chloride and 15 mM sodium citrate).

Specifically, examples of the DNA which hybridizes with a DNA having a base sequence represented by SEQ ID NO: 3 or 4 include a DNA having a base sequence having about 70% or more, preferably about 80% or more, more preferably about 90% or more, most preferably about 95% or more homology with a base sequence represented by SEQ ID NO: 3 or 4. Hybridization can be performed according to the known method such as the method described in Molecular Cloning, A laboratory Manual, Third Edition J. Sambrook et al., Cold Spring Harbor Lab. Press, 2001 (hereinafter, abbreviated as Molecular Cloning Third Edition). In addition, when a commercially available library is used, hybridization can be performed according to the method described in an attached instruction.

As a DNA encoding a partial peptide of HGF used in the present invention, any DNA may be used as far as it is a DNA having a base sequence encoding the aforementioned partial peptide. Like the DNA encoding HGF, a DNA encoding a partial peptide may be any one of a genome DNA, a genome DNA library, a cDNA derived from the aforementioned cell or tissue, a cDNA library derived from the aforementioned cell or tissue, and a synthetic DNA. A vector used in the library may be any one of bacteriophages, plasmids, cosmids, and phagemides. Alternatively, a DNA may be amplified using a mRNA fraction prepared from the aforementioned cell or tissue by a direct RT-PCR method. Examples of a specific DNA encoding a partial peptide of the present invention include (a) a DNA having a partial base sequence of a DNA having a base sequence represented by SEQ ID NO: 3 or 4, (b) a DNA which hybridizes with a DNA having a partial base sequence of a DNA having a base sequence represented by SEQ ID NO: 3 or 4 under stringent conditions, and encodes a protein having substantially the same quality of activity as that of HGF, and a DNA having a partial base sequence of the (a) or (b).

Also as an RNA encoding HGF or a partial peptide used in the present invention, any RNA may be used in the present invention and is in the scope of the present invention as far as it can express HGF or a partial peptide by a transcriptase. In addition, the RNA may be obtained by the known means.

As a means for cloning a DNA completely encoding HGF or a partial peptide used in the present invention (hereinafter, abbreviated as protein of the present invention in some cases), the DNA can be amplified using a synthetic DNA primer containing a partial base sequence of the protein of the present invention by a PCR method, or can be selected by hybridization using a DNA fragment or a synthetic DNA encoding a part or an entire region of labeled HGF among DNAs incorporated into a suitable vector. A hybridization method can be performed, for example, according to the method described in Molecular Cloning Third Edition. In addition, when a commercially available library is used, hybridization can be performed according to the method described in an attached instruction.

Alternatively, the DNA may be cloned by chemical synthesis from the known HGF base sequence information using the previously known method. Examples of the chemical synthesis method include a method of chemical synthesis with a DNA synthesizer such as a DNA synthesizer model 392 (manufactured by Perkin Elmer) utilizing a phosphoamidite method.

Substitution of a base sequence of a DNA can be performed by using PCR or the known kit such as Mutan™-superExpress Km (TAKARA SHUZO Co., Ltd.), and Mutan™-K (TAKARA SHUZO Co., Ltd.) by the known method such as the ODA-LA PCR method, the gapped duplex method, and the Kunkel method, or similar methods thereto. The cloned DNA encoding the protein of the present invention can be used as it is, or can be used after digestion with a restriction enzyme or after addition to a linker, if desired, depending on the purpose. The DNA may have ATG as a translation initiation codon on its 5'-end, and may have TAA, TGA or TAG as a translation termination codon on a 3'-end. These translation initiation codon and translation termination codon may be added using a suitable synthetic DNA adopter.

The DNA or RNA encoding HGF used in the present invention (hereinafter, abbreviated as DNA or the like of the present invention in some cases) may be modified in order to enhance its stability in a cell or reduce its toxicity if such DNA or RNA has toxicity. Examples of such modification include the methods described, for example, in J. Kawakami et al., Pharm Tech Japan, Vol. 8, p247(1992); Vol. 8, p395(1992); S. T. Crooke et al. ed., Antisense Research and Applications, CRC Press (1993). The DNA or the like of the present invention may be used in a special form where it is encapsulated in a liposome or a microsphere. In addition, other substances other than a base may be added to the DNA or the like encoding HGF used in the present invention. Examples of such other substances include a sugar; an acid or a base; a polycation compound such as polylysine which serves to neutralize a charge of a phosphate nucleus; and a hydrophobic substance such as a lipid (e.g. phospholipids, cholesterol, etc.) which enhances interaction with a cell membrane, or increases uptake of nucleic acids. Examples of preferable lipids to be added include cholesterol and a derivative thereof (e.g. cholesteryl chloroformate, cholic acid, etc.). The above other substance may be attached to 3'-end or 5'-end of nucleic acids, and can be attached via a base, a sugar or an intramolecular nucleoside linkage. The DNA or the like of the present invention has an end which has been chemically modified. Examples of a group modifying an end include a group for capping which is specifically disposed at 3'-end or 5'-end of nucleic acids, and arrests degradation with a nuclease such as exonuclease and RNase. Examples of such group for capping include a hydroxyl-protecting group known in the art including glycol such as polyethylene glycol and tetraethylene glycol, though they are not limited thereto.

The DNA encoding HGF or a partial peptide thereof used in the present invention may be contained in a recombinant expression vector.

As a recombinant expression vector, an expression vector which can express HGF or a partial peptide thereof is preferable.

The recombinant expression vector used in the present invention can be prepared, for example, by connecting a DNA fragment having a base sequence encoding HGF downstream of a promoter in a suitable expression vector.

The recombinant expression vector used includes preferably *Escherichia coli*-derived plasmids (e.g. pCR4, pCR2.1, pBR322, pBR325, pUC12, pUC13), *Bacillus subtilis*-derived plasmids (e.g. pUB10, pTP5, pC194), yeast-derived plasmids (e.g. pSH19, pSH15), bacteriophages such as λ phage, viruses such as retrovirus, adeno-associated virus (AAV), adenovirus, lentivirus, vaccinia virus, baculovirus, poxvirus, herpesvirus, herpes simplex virus, lentivirus (HIV), sendai virus, Epstein-Barr virus (EBV), vaccinia virus, poliovirus, sindbis virus, SV40, pA1-11, pXT1, pRc/CMV, pRc/RSV, and pcDNAI/Neo. Inter alia, the above viruses are preferable, and adeno-associated virus (AAV), adenovirus, retrovirus, poxvirus, herpes virus, herpes simplex virus, lentivirus (HIV), sendai virus, Epstein-Barr virus (EBV), vaccinia virus, poliovirus, sindbis virus, and SV40 are preferable. It is more preferable to use adeno-associated virus (AAV) or adenovirus. Various serotypes are present in adenovirus, and 2-type or 5-type human adenovirus is preferably used in the present invention.

As the promoter, any promoter may be used as far as it is a suitable promoter depending on a host used for expressing a gene. For example, when an animal cell is used as a host, examples of such promoter include an SRα promoter, an SV40 promoter, an LTR promoter, a CMV promoter, and an HSV-TK promoter. Among them, a CMV promoter and an SRα promoter are preferably used. When a host is a bacterium of genus *Escherichia*, a trp promoter, a lac promoter, a recA promoter, a λP$_L$ promoter, and a lpp promoter are preferable. When a host is a bacterium of genus *Bacillus*, an SPO1 promoter, an SPO2 promoter and a penP promoter are preferable. When a host is yeast, a PHO5 promoter, a PGK promoter, a GAP promoter and an ADH promoter are preferable. When a host is an insect cell, a polyhedrin promoter and a P10 promoter are preferable.

As an expression vector, in addition to the aforementioned vectors, there may be used vectors optionally having an enhancer, a splicing signal, a polyA addition signal, a selectable marker, or an SV40 replication origin, etc. Examples of the selectable marker include a dihydrofolate reductase (hereinafter, abbreviated as dhfr in some cases) gene (methotrexate (MTX) resistance), an ampicillin resistant gene (hereinafter, abbreviated as Amp$^r$ in some cases), and a neomysin resistant gene (hereinafter, abbreviated as Neo$^r$ in some cases, G418 resistance). Particularly, when a dhfr gene is used as a selectable marker employing dhfr gene-defective Chinese hamster CHO cell, an objective gene may be selected by a medium containing no thymidine. Alternatively, if desired, a signal sequence adoptable to a host may be added to an expression vector. When the host is a bacterium of genus *Escherichia*, a PhoA signal sequence, and an OmpA signal sequence, etc. can be utilized. When the host is a bacterium of genus *Bacillus*, an α-amylase signal sequence, and a subtilisine signal sequence, etc. can be utilized. When the host is yeast, an MFα signal sequence, an SUC2 signal sequence, etc. can be utilized. When the host is an animal cell, an insulin signal sequence, an α-interferon signal sequence, and an antibody molecule signal sequence, etc. can be utilized. By introducing the thus constructed expression vector containing a DNA encoding a protein of the present invention into a vector, a transformant can be prepared.

The recombinant expression vector containing a DNA encoding HGF or a partial peptide thereof may be further introduced into a host cell.

As a host for the recombinant expression vector, for example, *Escherichia* bacteria, *Bacillus* bacteria, bifidobacteria, lacetic acid bacteria, yeast, insect cells, insects, and animal cells are used. Specific examples of *Escherichia* bacteria used include *Escherichia coli* K12/DH1 [Proc. Natl. Acad. Sci. USA, vol. 60, 160 (1968)], JM103 [Nucleic Acids Research, vol. 9, 309 (1981)], JA221 [Journal of Molecular Biology, vol. 120, 517 (1978)], HB101 [Journal of Molecular Biology, vol. 41, 459 (1969)], C600 [Genetics, vol. 39, 440 (1954)], DH5α [Inoue, H., Nojima, H. and Okayama, H., Gene, 96, 23-28 (1990)], and DH10B [Proc. Natl. Acad. Sci. USA, vol. 87, 4645-4649 (1990)]. As *Bacillus* bacteria, for example, *Bacillus subtilis* MI114 (Gene, vol. 24, 255(1983), [Journal of Biochemistry, vol. 95, 87(1984)] is used. Example of bifidobacteria include *Bifidobacterium longum, Bifidobacterium bifidum*, and *Bifidobacterium breve*. Examples of lacetic acid bacteria include *Lactobacillus, Streptococcus, Leuconostoc,* and *Pediococcus*. As yeast, for example, *Saccharomyces cerevisiae* AH22, AH22R$^-$, NA87-11A, DKD-5D, 20B-12, *Schizosaccharomyces pombe* NCYC1913, NCYC2036, and *Pichia pastoris* are used.

As an insect cell, for example, when a virus is AcNPV, an established cell derived from a larva of a cabbage armyworm (*Spodoptera frugiperda* cell; Sf cell), an MG1 cell derived from the midgut of *Trichoplusia ni*, a High Five™ cell derived from an egg of *Trichoplusia ni*, a cell derived from Mamestra-brassicae, or a cell derived from *Estigmena acrea* is used. When a virus is BmNPV, an established cell derived from silkworm (*Bombyx mori* N; BmN cell), etc. is used. As the Sf cell, for example, an Sf9 cell (ATCC CRL1711), and an Sf21 cell [all, Vaughn, J. L. et al., In Vivo, 13, p213-217 (1977)] are used. As an insect, for example, a larva of silkworm is used [Maeda et al., Nature, 315, 592 (1985)].

As an animal cell, for example, a monkey cell COS-7, a Vero cell, a Chinese hamster cell CHO (hereinafter, abbreviated as CHO cell), a dhfr gene-defective Chinese hamster cell CHO (hereinafter, abbreviated as CHO (dhfr$^-$) cell), a mouse L cell, a mouse AtT-20 cell, a mouse myeloma cell, a rat GH3 cell, and a human FL cell are used.

Transformation of bacterial of genus *Escherichia* can be performed according to the method described, for example, in Proc. Natl. Acad. Sci. USA, 69, p2110 (1972) and Gene, 17, p107 (1982). Transformation of bacteria of genus *Bacillus* can be performed according to the method described, for example, in Molecular & General Genetics, 168, p111 (1979). Transformation of yeast can be performed according to the method described, for example, in Methods in Enzymology, vol. 194, p182-187 (1991), Proc. Natl. Acad. Sci. USA, 75, p1929 (1978).

Transformation of insect cells or insects can be performed according to the method described, for example, in Bio/Technology, 6, p47-55 (1988). Transformation of an animal cell can be performed according to the method described, for example, in Cell Technology Separate Volume 8 New Cell Technology Experimental Protocol, p263-267 (1995) (Published by Shujunsha Co., Ltd.), and Virology, vol. 52, p456 (1973). Like this, a transformant transformed with the expression vector containing a DNA encoding a protein of the present invention is obtained. When a transformant having a host of bacteria of genus *Escherichia* or *Bacillus* is cultured, a liquid medium is suitable as a medium to be used in culturing, and a carbon source, a nitrogen source, inorganic substances and other substances necessary for the growth of the transformant are contained therein. Examples of carbon sources include glucose, dextrin, soluble starch, and sucrose. Examples of nitrogen sources include inorganic or organic substances such as ammonium salts, nitrates, corn steep liquor, peptone, casein, meat extract, soybean meal, and potato extract. Examples of inorganic substances include calcium chloride, sodium dihydrogen phosphate, and magnesium chloride. Alternatively, yeast extract, vitamins, and growth promoting factor, etc. may be added. The pH of the medium is desirably about 5 to 8.

As a medium for culturing bacteria of genus *Escherichia*, for example, an M9 medium containing glucose and casamino acid [Miller, Journal of Experiments in Molecular Genetics, p431-433, Cold Spring Harbor Laboratory, New York (1972)] is preferable. Herein, if necessary, in order to make a promoter work effectively, a drug such as 3β-indolylacrylic acid can be added. When a host is bacteria of genus *Escherichia*, culturing is performed usually at about 15 to 43° C. for about 3 to 24 hours, and if necessary, aeration or stirring may be carried out. When a host is bacteria of genus *Bacillus*, culturing is performed usually at about 30 to 40° C. for about 6 to 24 hours and, if necessary, aeration or stirring may be performed. When a transformant having a host of yeast is cultured, examples of a medium include a Burkholder minimum medium [Bostian, K. L et al., Proc. Natl. Acad. Sci. USA, 77, p4505 (1980)] and an SD medium containing 0.5% casamino acid [Bitter, G. A. et al., Proc. Natl. Acad. Sci. USA, 81, p5330(1984)]. It is preferable that the medium pH is adjusted to about 5 to 8. Culturing is performed usually at about 20° C. to 35° C. for about 24 to 72 hours, and aeration or stirring is optionally carried out.

When a transformant having a host of insect cells or insects is cultured, a medium in which an additive such as immobilized 10% bovine serum is appropriately added to Grace's Insect Medium [Grace, T. C. C., Nature, 195, p788 (1962)] is used as a medium. It is preferable that the medium pH is adjusted to about 6.2 to 6.4. Culturing is performed usually at about 27° C. for about 3 to 5 days, and aeration or stirring is performed if necessary. When a transformant having a host of animal cells is cultured, for example, an MEM medium containing about 5 to 20% fetal bovine serum [Science, 122, p501 (1952)], a DMEM medium [Virology, 8, p396 (1959)], a RPMI 1640 medium [The Journal of the American Medical Association, 199, p519 (1967)], and a 199 medium [Proceeding of the Society for the Biological Medicine, 73, p1 (1950)] are used as a medium. It is preferable that the pH of such medium is about 6 to 8. Culturing is performed usually at about 30° C. to 40° C. for about 15 to 60 hours, and if necessary, aeration or stirring is carried out.

As described above, HGF can be produced in cells or cell membranes or outside the cells of transformants, and HGF can be effectively administered to a living body.

A recombinant expression vector as a naked vector may be introduced into a living body in vivo without transformation into a host cell, and this may be used in the present invention. In using the naked vector, the recombinant expression vector to be used includes a plasmid such as pCAGGS [Gene, 108, p193-200 (1991)], pBK-CMV, pcDNA3.1, and pZeoSV (Invitrogen Corp., Strategene Inc.) can be used. The vector may contain the aforementioned SRα promoter, SV40 promoter or the like, and optionally, an enhancer, a splicing signal, a polyA addition signal, a selectable marker, and an SV40 replication origin.

Alternatively, a DNA encoding HGF or a recombinant expression vector containing a DNA encoding HGF may be contained in an artificial vector such as a liposome, a microcapsule, a cytofectin, a DNA-protein complex, and a biopolymer.

A liposome is a closed vesicle composed of a lipid bilayer membrane having an aqueous layer in an interior thereof, and it is known that the lipid bimolecular membrane structure is extremely approximate to a biomembrane. Examples of phospholipids to be used in the production of liposomes include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A liposome can be prepared according to the method known per se. As a liposome, a membrane-fused liposome, a HVJ-membrane-fused liposome [Kaneda. Y et al., Biol. Chem., 264, p12126-12129 (1989), Kato. K et al., Biol. Chem., 266, p3361-3364 (1991), Tomita. N et al., Biochem. Biophys. Res., 186, p129-134 (1992), Tomota. N et al., Cric. Res., 73, p898-905 (1993)], and a cationic liposome (JP-A No. 2000-510151, JP-A No. 2000-516630) are known. It is particularly preferable to use a HVJ-membrane-fused liposome which is fused with Sendai virus (HVJ). When a glycoprotein of HVJ is incorporated in or covalently bound to a surface of a liposome, and polyethylene glycol, etc. is added, an efficiency of introducing a gene into a cell is increased.

A preventive or therapeutic agent for asthma of the present invention can be obtained by inclusion in a liposome of a DNA in which a signal sequence, a promoter and a polyadenylation sequence are added to a DNA encoding HGF, or by inclusion in a liposome of a recombinant expression vector containing a DNA encoding HGF.

A microcapsule is a particle coated with a film, and is composed of particles coated with a coating material consisting of a mixture of a film forming polymer derivative, a hydrophobic plasticizer, a surface activating agent or/and a lubricant nitrogen-containing polymer.

A preventive or therapeutic agent for asthma of the present invention can be obtained by inclusion in a microcapsule of a DNA in which a signal sequence, a promoter and a polyadenylation sequence are added to a DNA encoding HGF, or by inclusion in a microcapsule of a recombinant expression vector having a DNA encoding HGF.

By directly administering HGF or a salt thereof, or administering a DNA encoding HGF to express HGF at an administration site, inflammation such as bronchitis of an administered living body can be suppressed. Therefore, (a) HGF or a partial peptide thereof or a salt thereof, or (b) a DNA or an RNA encoding HGF or a partial peptide thereof can be used as a preventive or therapeutic agent for asthma.

The "asthma" refers to a series of syndrome associated with so-called allergy chronic airway inflammation and airway hyperresponsiveness (AHR). The preventive or therapeutic agent for asthma of the present invention is effective in both of acute/transient or chronic asthma, and exerts the effect also in child asthma. When a cause for asthma is any one of virus infection (so-called cold), allergen, and chemical substance, or whether atopic or non-atopic, particularly, in child asthma, the present agent can be effectively used for preventing or treating them.

When the preventive or therapeutic agent for asthma of the present invention comprises HGF, the agent can be formulated into a preparation according to the conventional manner. On the other hand, when a DNA encoding HGF is used as the preventive or therapeutic agent, the DNA alone, or after the DNA is inserted into a suitable vector such as a retrovirus vector, an adenovirus vector, a lentivirus vector, and an adenovirus-associated virus vector as described above, may be formulated into a preparation according to the conventional manner. The DNA or the like of the present invention may be administered as it is or together with an auxiliary agent for promoting uptake by a gene gun or a catheter such as a hydrogel catheter.

For example, HGF or a salt thereof, or a DNA encoding HGF may be orally administered in the form of an optionally sugar-coated tablet, a capsule, an elixir agent or a microcapsule, or may be embedded into an affected part or subcutaneously or intramuscularly. Alternatively, it can be administered parenterally in the form of an injection such as sterile solution or suspension with water or other pharmaceutically acceptable solution. The preventive or therapeutic agent for asthma of the present invention can be administered in the form of a nebulizer or inhalant (pocket-type nebulizer). In the nebulizer administration, a motor-driven nebulizer (e.g. jet-type nebulizer, ultrasound-type nebulizer, mesh-type nebulizer, etc.) is preferably used. The preventive or therapeutic agent for asthma of the present invention is placed into a motor-driven nebulizer device, a liquid is converted into a mist by ejection of a pressurized air, and the mist is sprayed into the human airway, or a drug is sprayed into the airway by ultrasound vibration.

Examples of a method for inhalant administration include a method of directly spraying the preventive or therapeutic agent for asthma of the present invention, for example, with a spray, and a method of inhaling a drug sprayed using an inhalation auxiliary instrument (spacer).

The preparation of the present invention can be prepared by kneading HGF or a salt thereof or a DNA encoding HGF with a physiologically recognized known carrier, flavor, excipient, vehicle, antiseptic, stabilizer, binder, or substance imparting sustained-release.

Examples of additives which can be kneaded in a tablet or a capsule include a binder such as gelatin, corn starch, tragacanth, and gum arabic; an excipient such as crystalline cellulose; a swelling agent such as corn starch, gelatin, and alginic acid; a lubricant such as magnesium stearate; a sweetener such as sucrose, lactose, and saccharin; a flavor such as peppermint, oil from *Gaultheria adenothrix*, and cherry. A tablet may be coated with a suitable coating agent (gelatin, white sugar, gum arabic, carnauba wax, etc.), or an enteric coating agent (e.g. cellulose acetate phthalate, methacrylic acid copolymer, hydroxypropylcellulose phthalate, carboxymethylethylcellulose, etc.). In the case of a capsule, further, a liquid carrier such as an oil and fat may be contained. In addition, a capsule may be an enteric-coated capsule, an gastric resistant capsule, or a release-controlled capsule in addition to the conventional capsules. When formulated into an enteric capsule, HGF coated with an enteric coating agent, or a mixture obtained by adding the aforementioned suitable excipient to HGF is filled into a conventional capsule. Alternatively, HGF or a mixture obtained by adding the aforementioned suitable excipient to HGF may be filled into a capsule coated with an enteric coating agent or a capsule formed using a base of an enteric polymer.

A sterile composition for injection can be formulated according to the conventional formulation practice such as dissolution or suspension formation of an active ingredient in an aqueous solution or an oily solution for injection. As an aqueous solution for injection, for example, an isotonic containing physiological saline, glucose and other auxiliary drug (e.g. D-sorbitol, D-mannitol, sodium chloride, etc.) is used. Further, a suitable solubilizer such as an alcohol (e.g. ethanol), a polyalcohol (e.g. propylene glycol, polyethylene glycol), and a nonionic surfactant (e.g. Polysorbate 80™, HCO-50) may be used in combination thereof. As an oily solution, for example, a sesame oil or a soybean oil is used, and a solubilizer such as benzyl benzoate and benzyl alcohol may be used in combination thereof. Further, for example, a buffer (e.g. phosphate buffer, sodium acetate buffer), a soothing agent (e.g. benzalkonium chloride, procaine hydrochloride, etc.), a stabilizer (e.g. human serum albumin, polyethylene glycol, etc.), a preservative (e.g. benzyl alcohol, phenol, etc.), and an antioxidant may be blended in the aforementioned sterile composition. The prepared sterile composition is usually filled into an appropriate ample, and this is served as an injectable solution.

In addition, when prepared as a solution or an inhalant for a nebulizer, any additive may be used as far as it is an additive which is generally used for an inhalation preparation. For example, the aforementioned excipient, buffer, solubilizer, preservative, stabilizer, isotonic agent, pH adjusting agent (hydrochloric agent, sodium hydrochloride, etc.), and corrective (citric acid, menthol, glycyrrhizin ammonium salt, glycine, flavor, etc.) are used. In the inhalant preparation, a propellant is incorporated in addition to the aforementioned additive. As the propellant, a liquefied gas propellant and a compressed gas, etc. are used. Examples of the liquefied gas propellant include fluorinated hydrocarbons (alternative flon such as HCFC22, HCFC-123, HCFC-134a, HCFC142, etc.), liquefied petroleum, and dimethyl ether. Examples of the compressed gas include a soluble gas (carbon dioxide gas, nitrous oxide gas, etc.), and an insoluble gas (nitrogen gas, etc.).

Since the thus obtained preparation is safe and low toxic, it can be administered, for example, to a mammal (e.g. human, rat, mouse, rabbit, sheep, pig, cow, cat, dog, monkey, etc.).

When a DNA encoding HGF used in the present invention is administered to a living body without formulating into a preparation, administration may be performed according to the known method, but there are an in vivo method of directly introducing a DNA in a body, and an ex vivo method of taking out a certain cell extracorporeally from a human, etc. to be administered, introducing a DNA into the cell, and returning the transformed cell into a body [Nikkei Science, No. April, 20-45 (1994), Gekkan Yakuji, 36, 23-48 (1994), Experimental Medicine Extra Edition, 12, 15 (1994)]. Examples of a method of introducing a DNA into a cell in those methods include a method of introducing into a cell by the methods known per se such as a gene introducing method of permitting a DNA to be contained in a recombinant expression vector such as an adeno-associated virus vector, an adenovirus vector and a retrovirus vector, and introducing such expression vector as described above and a method of introducing a DNA into a cell by transfection, electroporation, microinjection, transduction, cell fusion, DEAE dextran, calcium phosphate precipitation, or a gene gun together with a carrier (metal particle etc.) [Wu et al., J. Biol. Chem. 267, 963-967 (1992), Wu et al., J. Biol. Chem. 263, 14621-14624, (1988), Proc. Natl. Acad. Sci., USA, 88, 2726-2730 (1991)]. In addition, when a liposome is used, examples of DNA introduction include the liposome method, the HVJ-liposome method, the cationic liposome method, the lipofectin method, and the lipofectamine method.

Inter alia, from a viewpoint of introduction efficiency, the gene introducing method using an adenovirus vector or a retrovirus vector is desirable.

Alternatively, the aforementioned recombinant expression vector is introduced into a host cell, and the transformant may be used as a preventive or therapeutic agent of the present invention. In this case, for example, the transformant is contained in a capsule, and can be administered to a living body in the form of a capsule preparation.

In addition, when a liposome such as an HVJ-liposome is used, it can be formulated into a liposome preparation such as suspensions, frozen preparations, and centrifugation-concentrated frozen preparations.

The preventive or therapeutic agent for asthma of the present invention can be orally administered, or embedded into an affected part or subcutaneously or intramuscularly, or administered intravenously, and it is preferable that the agent is administered intravenously or administered locally into a bronchia.

In addition, it is preferable that the preventive or therapeutic agent for asthma of the present invention is administered when the symptom of asthma occurs. Alternatively, when there is a risk leading to chronic, severe or refractory asthma, it is preferable that the agent is continuously administered to prevent incomplete repair of the airway (remodeling).

Since a dose of the preventive or therapeutic agent of the present invention is different depending on administration subject, symptom, dosage form, and treatment term, it cannot be generally said. Usually, in the case of intravenous administration, the dose as HGF is about 250 to 1000 µg/Kg/day, preferably about 300 to 800 µg/Kg/day, particularly preferably about 300 to 550 µg/Kg/day, or the dose as a DNA encoding HGF is about 0.2 to 40,000 µg/Kg/day, preferably about 2 to 2,000 µg/Kg/day.

By administering the preparation of the present invention, inflammation of the airway at attack of asthma can be suppressed and prevented. It is thought that a change such as "constriction of bronchial smooth muscle", "edema of mucosa", and "increase in secreta" usually occurs at inflammation of the airway. As specific symptom, respiratory pause is seen. From a viewpoint of pathomorphology, asthma can be confirmed by invasion of inflammation cells such as eosinophils, T lymphocytes and macrophages into the lung tissue, or excessive growth of mucus-producing cells (goblet cell) in the airway epithelial tissue. In addition, an antigen-specific IgE value in serum is increased, and it has been confirmed that the concentration of Th2 cytokines such as IL-4, IL-5, and IL-13, or growth factors such as platelet-derived growth factor (PDGF), nerve growth factor (NGF), and transformation growth factor (TGF-β) in a bronchoalveolar lavage fluid (hereinafter, abbreviated as BAL fluid in some cases) further increases.

Therefore, when the preparation of the present invention is administered, the aforementioned phenomena seen at inflammation are suppressed.

The airway inflammation suppressing action and effect of the preparation of the present invention can be confirmed by making an experimental model of bronchial asthma by antigen repetitive inhalation exposure using mice, and placing the mice under environment where an inflammation reaction of the airway is caused, administering the preparation of the present invention to the mice, so that airway inflammation and airway hyperresponsiveness are suppressed.

Although there is no particular limitation for the method of making a model of bronchial asthma, examples of such method include a method of subjecting a mouse to ovalbumin sensitization/inhalation exposure to impart antigen-specific immunity. The airway inflammation can be caused by allowing a model mouse of antigen-induced allergic airway inflammation to inhale a substance having the airway constricting action, such as methacholine.

For measuring a serum antigen-specific IgE value, for example, an ELISA method (Temann, U. A., Am. J. Respir. Cull. Mol. Biol., 16, p471-478, 1997) can be used.

Measurement of the number of total BAL cells including inflammation cells in a BAL fluid can be performed, for example, by washing alveoli with a physiological saline, and counting the number of cells present in the resulting BAL fluid under a microscope.

Measurement of a concentration of cytokines such as IL-4, IL-5, and IL-13, or growth factors such as PDGF, NGF, and TGF-β in a supernatant of a BAL fluid can be performed, for example, by an ELISA method. It is better to perform colorimeter measurement in ELISA according to the method described in each attached instruction.

Examples of a method of confirming airway inflammation histologically and immunohistologically include a method of counting the number of mucus-producing cells (goblet cell) under a microscope after staining of a lung tissue surrounding a bronchia with periodic acid-Schiff, and a method of counting the number of eosinophils, lymphocytes or macrophages similarly under a microscope after staining of a tissue cell surrounding the bronchia with hematoxylin-eosin. In these countings, NIH Image Analysis system (National Institute of Health, Bethesda, Md.) can be used. In addition, accumulation of TGF-β in the cells can be confirmed, for example, by adsorbing anti-TGF-β rabbit IgG onto a tissue cell surrounding the bronchia and, thereafter, performing avidin-biotin treatment (Ueki, T., et al. Nat. Med., 5, p226-230, 1999).

The present invention will be specifically explained by way of Examples, but it goes without saying that the present invention is not limited to them.

MANUFACTURING EXAMPLE

Manufacturing of Preparation Containing HGF (1) Preparation of HGF cDNA

A mRNA was isolated from human MRC-5 fibroblasts using Fast Track mRNA isolation kit (Invitrogen), and this was used to perform RT-PCR (reverse transcription/polymerase chain reaction) to isolate HGF cDNA. Specifically, 0.5 μL (150 ng) of a mRNA solution, 5 μL of a 10×RT-PCR solution (500 mM KCl, 100 mM Tris-HCl (pH 9.0), 1% Triton X-100, 15 mM MgCl$_2$), 4 μL of dNTP (2.5 mM), 2 μl of a primer: a (10 mM), 2 μL of a primer: b (10 mM), 0.5 μL of Taq polymerase (Takara), 0.5 μL of RNasin (Promega), 0.5 μL of a reverse transcriptase (Takara) and 35.2 μL of DEPC-treated H$_2$O were mixed, a reverse transcription reaction was performed at 42° C. for 30 minutes and at 95° C. for 5 minutes, a cycle of 94° C. for 30 seconds, 55° C. for 1 minute and 72° C. for 1 minute was repeated 40 times, and this was further reacted at 72° C. for 7 minutes to obtain HGF cDNA. The thus obtained HGF cDNA was cloned into pCRII™ vector using TA Cloning Kit (Invitrogen) to obtain pCRII/HGF.

Sequences of a primer: a and a primer: b are as follows:

```
                                           (SEQ ID NO: 5)
Primer: a;    5'-CCCGTCCAGCGGTACCATGTGGGTGACC-3'

(SEQ ID NO.: 6)
Primer: b;    5'-TACGGGATGGACTAGTTAGACTATTGTAG-3'
```

(2) Construction of Recombinant Expression Vector

The HGF cDNA incorporated into the pCRII vector prepared in (1) was cut with a restriction enzyme Kpn I/Spe I, and a cut terminal was blunt-ended by T4 DNA polymerase (Takara) treatment. The resulting HGF cDNA fragment was treated with a restriction enzyme Xho I in advance, mixed with the CHO cell expression vector pCAGGS-DHFR in which the cut terminus had been blunt-ended, and ligated with T4 DNA ligase to obtain an HGF expression vector, pCAGGS-DHFR/HGF. The resulting HGF expression vector has the HGF cDNA between a chicken β-actin promoter and a rabbit β-globin poly(A) signal sequence. In addition, selection of the transformed cell becomes possible by a DHFR chimera gene ligated to a mouse dihydrofolate reductase (DHFR) gene with a cytomegalovirus early promoter and a poly(A) signal sequence.

(3) Transformation into Chinese Hamster CHO Cells and Expression Thereof

The CHO cell expression vector, pCAGGS-DHFR/HGF was introduced into a DHFR-defective cell of Chinese hamster CHO cells by the method of Wigler et al. [Cell, 11, p233 (1977)]. About 30 μg of the pCAGGS-DHFR/HGF plasmid was dissolved in each 240 μL of 0.5 M calcium chloride, and 240 μL of a 2×HEPES buffer (pH 7.1) comprising 20 mM HEPES, 280 mM sodium chloride and 1.5 mM sodium phosphate was added with stirring. Stirring was continued at room temperature for 30 minutes to form a coprecipitate of the plasmid and calcium phosphate. Subsequently, 5×10$^5$ CHO cells were cultured at 37° C. for 24 hours under 5% CO$_2$ using an α-MEM medium (Flow Laboratory) containing 10% bovine fetal serum (Gibco) and 1% glutamine. After medium exchange, the coprecipitate of the plasmid and calcium phosphate was added, and this was allowed to stand at room temperature for 20 minutes. Further, after incubation at 37° C. for 4 hours, the medium was removed, a 1×HEPES buffer with 15% glycerin added thereto was added, and this was allowed to stand at room temperature for 5 minutes. After cells were washed with a medium, the medium was exchanged, and this was cultured at 37° C. for 7 days to obtain a transformed cell. The resulting cell strain did not contain a ribonucleoside and a deoxyribonucleoside, and in order to obtain a stable HGF-highly producing strain using an α-MEM medium (Flow Laboratory) containing dialyzed 10% bovine fetal serum (Gibco) and 2% glutamine, passage culturing was repeated on the same medium by successively increasing a methotrexate concentration of 100 nM, 250 nM, 500 nM, 750 nM, 1 μM and 2 μM. Clone selection of the resulting HGF-producing recombinant cells was performed to obtain a stable HGF-producing strain.

(4) Purification of HGF from Supernatant of Transformed CHO Cell Culture

The HGF-producing Chinese hamster CHO recombinant cell strain obtained in the above (3) was cultured in an α-MEM medium (Flow Laboratory) which does not contain a ribonucleoside and a deoxyribonucleoside, and contains 10% bovine fetal serum (Gibco), 1% glutamine and 2 µM methotrexate, and HGF was purified from the culture supernatant.

a) Heparin Affinity Chromatography

Tween 80 was added to 12 L of a culturing solution of the HGF-producing Chinese hamster CHO recombinant cell strain to a final concentration of 0.01%, and this was filtered with a Sterivex HV filter (Millipore Japan Ltd.). This was added to heparin-Sepharose CL-6B (manufactured by Pharmacia; column volume 50 mL) equilibrated with a buffer A (20 mM Citrate-NaOH, 0.01% Tween80, pH 6.5) containing 0.15 M sodium chloride. After washed with a buffer A containing 0.5 M sodium chloride, peak fractions eluted by a linear concentration gradient with 0.5 M to 2.5 M sodium chloride were collected to obtain a heparin eluate A.

b) Anionic Exchange Chromatography

The heparin eluate A was dialyzed with a 100-fold volume of a buffer B (20 mM Tris-HCl, 0.01% Tween 80, pH8.0) three times, and added to DEAE-Sepharose (manufactured by Pharmacia, column volume 40 mL) equilibrated with a buffer B. After washed with a buffer B, peak fractions eluted with a buffer B containing 1 M sodium chloride were collected to obtain a DEAE eluate.

c) Heparin Affinity Chromatography (Second Time)

The DEAE eluate was dialyzed three times with a 100-fold volume of a buffer A, and added to heparin-Sepharose CL-6B (manufactured by Pharmacia, column volume 50 mL) equilibrated with a buffer A containing 0.15 M sodium chloride. After washed with a buffer A containing 0.3 M sodium chloride, adsorbed substances were eluted by a linear concentration gradient with 0.3 M to 2.5 M sodium chloride. Peak fractions of HGF were collected to obtain a heparin eluate B. The yield of purified HGF was about 12 mg, and the recovery rate from the culture supernatant was about 50%.

d) SDS-polyacrylamide Electrophoresis

HGF was subjected to SDS-polyacrylamide electrophoresis under reduction and non-reduction by 2-mercaptoethanol. Purified HGF indicated about 50 kDa at [2-ME(−)] under non-reducing condition, and indicated about 67 kDa at [2-ME (+)] under reducing condition.

(5) Production of Lyophilized Preparation

A solution containing HGF (1 g) prepared in (4), mannitol (1 g) and Polysorbate 80 (10 mg) in 100 mL of a physiological saline was sterilely prepared, each 1 mL was dispensed in a vial, and this was lyophilized, and sealed to produce a preparation of the present invention as a lyophilized preparation (Preparation 1).

EXAMPLES (1) Confirmation of Airway Inflammation Suppressing Effect by HGF Administration Influence of HGF administration in airway hyperresponsiveness.

A diet not containing ovalbumin (OVA) was fed to female 8 to 10 week-old mice (BALB/c:Charles River Japan, Inc.), and the mice were reared at a constant temperature under constant light cycle.

A model mouse of bronchial asthma was made by the following method. Twenty µg of OVA (Grade V, Sigma, St. Louis Mo.) and 2.25 mg of aluminum sulfate (emulsifier: AlumImuject; Piearce, Rockford, Ill.) were suspended in 100 µL of a physiological saline, and this suspension was intraperitoneally administered to a mouse 0 day and 14 days after the initiation of feeding. The mouse inhaled OVA for 20 minutes from a solution containing 1% OVA in a physiological saline using an ultrasound nebulizer. Inhalation exposure was performed 28, 29 and 30 days after the initiation of feeding.

During the production of the model mice of bronchial asthma, the preparation 1 obtained in Manufacturing Example was administered to a part of mice. One mg of the preparation 1 was dissolved and diluted in 10 mL of a physiological saline, and 0.2 mL of the solution was continuously administered subcutaneously every day on $27^{th}$ to $31^{st}$ day after the initiation of feeding (HGF-administered group, n=16:sensitized/exposed+HGF). The dose of the preparation 1 was 500 µg/kg/day as HGF.

A group to which 0.2 mL of a physiological saline in place of a solution made by dissolving the preparation 1 in a physiological saline was continuously administered subcutaneously on $27^{th}$ to $31^{st}$ day after the initiation of feeding was also prepared (physiological saline-administered group, n=16: sensitized/exposed+physiological saline). In addition, mice which were not subjected to the sensitization/exposure with OVA were designated as a control group (n=16:non-sensitized/non-exposed).

Comparison between groups was carried out by performing two-way analysis of variance, and testing a difference between a physiological saline-administered group and an HGF-administered group (*), or between a control group and a physiological saline-administered group (#) (t test). In the following test, comparison between groups was performed similarly.

Assessment of airway hypersensitivity in a model mouse of bronchial asthma was performed by the following method. A methacholine-containing physiological saline (3.125 to 25 mg/mL) or only a physiological saline was inhaled for 3 minutes respectively in an HGF-administered group, a physiological saline-administered group and a control group having no bronchial asthma of bronchial asthma model mice using an ultrasound nebulizer (NE-U07, manufactured by OMRON), mice were placed into a whole body plethysmography box, and airway hypersensitivity (Penh) was measured using computer respiration function analyzing system (Buxco Electronics Inc., Troy, N.Y.) with Barometric plethysmography (Barometric plethysmography: Buxco Electronics Inc, Troy, N.Y.) in the state where mice were conscious and unrestrained. Measurement of Penh was according to the following equation.

$$Penh = PEP/PIP \times Te - Tr/Tr$$

PEP; peak expiratory pressure (mL/s), maximal positive box pressure occurring in one breath PIP; peak inspiratory pressure (mL/s), maximal negative box pressure occurring in one breath Te; expiratory time (s), time from end of inspiration to start of next inspiration Tr; relaxation time (s), time of the pressure decay to 36% of total box pressure during expirations

[Cieslewicz. G et al., JCI, 104, p301-308 (1999)].

As a result, in each group, there was a slight difference in a base line Penh value obtained at inhalation of only a physiological saline (non-sensitized/non-exposed: 0.49±0.04, sensitized/exposed+physiological saline: 0.53±0.17, sensitized/exposed+HGF: 0.53±0.13), while when methacholine was inhaled, rapid increase in airway hypersensitivity was seen depending on a methacholine concentration in a physiological saline-administered group. To the contrary, in an HGF-administered group, the increase in airway hypersensitivity was significantly suppressed (FIG. 1).

(2) Measurement of Number of Inflammation Cells in BAL Fluid

Forty eight hours after the test described in (1), the interior of bronchia/alveoli of mice of each group washed two times with a physiological saline (1 mL, 37° C.) via an intrabronchial tube. The lavage was recovered, and the total amount of BAL fluid and the total number of cells in the BAL fluid were measured using a Burker-türk type hemocytometer plate. Then, a monolayer specimen was prepared (4,000 rpm, 5 minutes) from the BAL fluid using Cytospin3 (manufactured by SHANDON), and this was May-Giemsa-stained (13 minutes). The tissue monolayer specimen was observed under a microscope, and the number of inflammation cells such as macrophages, lymphocytes, neutrophils, and eosinophils in the BAL fluid was measured.

Figure 2:
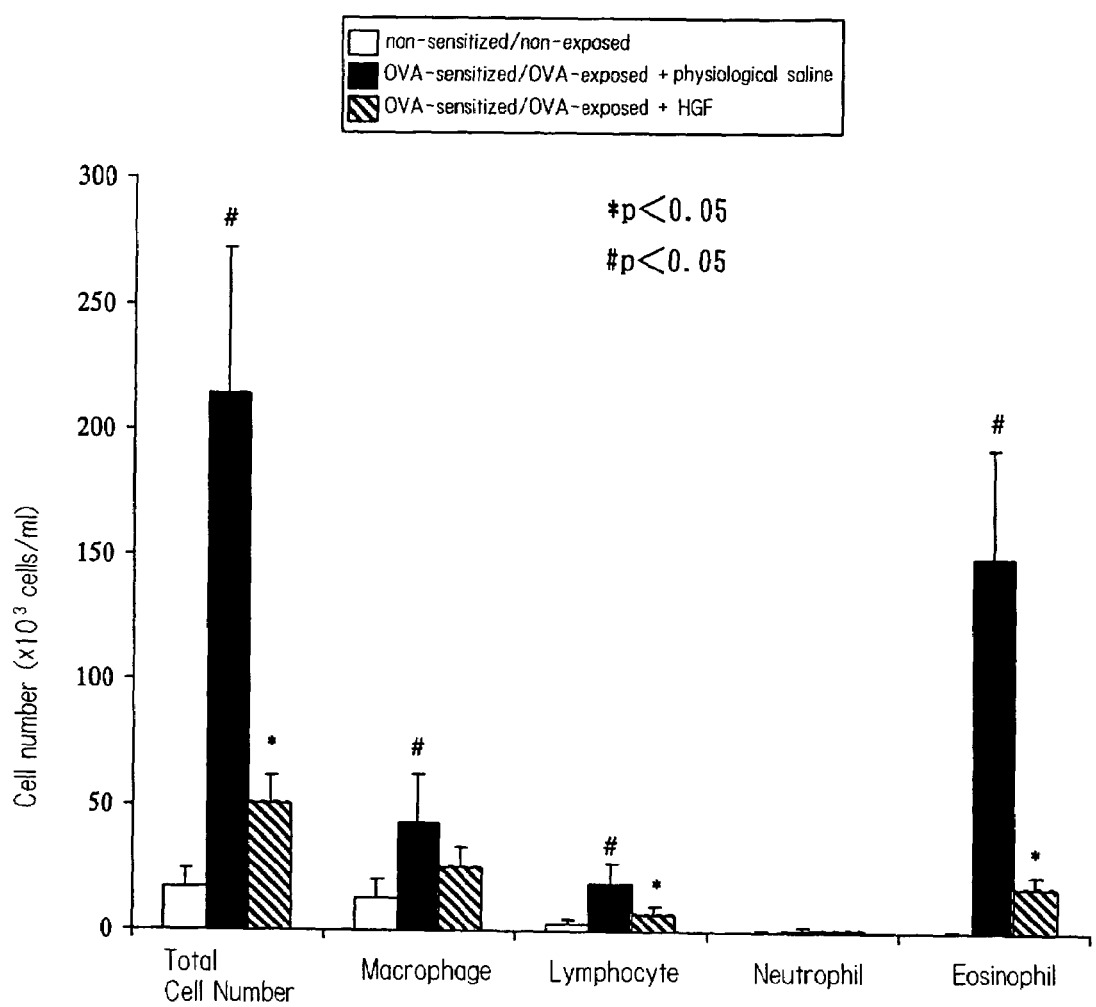
FIG. 2 is a view showing influence of HGF administration on increase in the number of inflammation cells in a bronchoalveolar lavage fluid (hereinafter, abbreviated as BAL fluid in some cases) in a model mouse of bronchial asthma 48 hours after antigen inhalation exposure.

As a result, in the control group, the total number of BAL cells was small, and about 95% or more of the cells was occupied by macrophages, and other inflammation cells were hardly seen. In the physiological saline-administered group, remarkable increase in lymphocytes and eosinophils was seen. To the contrary, in the HGF-administered group, increase in the number of lymphocytes and eosinophils seen in the physiological saline-administered group was significantly suppressed (FIG. 2).

(3) Measurement of Number of Invasion of Inflammation Cells in Tissues Surrounding Bronchi/Vessels Two mL of the air was supplied to the right lung after washing the interior of the alveoli of (2) via an intrabronchial tube, and the right alveoli were swollen and fixed with 10% formalin for 48 hours. A lung tissue block surrounding main bronchi was excised from this fixed tissue, and was fixed with paraffin. A tissue piece having a thickness of 4 μm was prepared from the block, and fixed on a microscope slide, and paraffin was then removed. The tissue specimen slide was stained with hematoxylin-eosin, and the invasion situation of visualized inflammation cells was observed under a microscope (final magnification×400, inset×1,000). For counting the number of inflammation cells, NIH Image Analysis system (National Institute of Health, Bethesda, Md.) was used. The counting was performed for randomly selected ten fields, and an average of the number of cells per tissue 1 mm$^2$ was calculated. The number of mice in each group subjected to the test was 16.

Hematoxylin-eosin staining was performed as follows. A tissue specimen slide was deparaffined, and stained with a hematoxylin solution at room temperature for 5 minutes, and an excessive dye washed off by immersing in tepid water at 37° C. for 5 minutes. Then, the specimen was immersed in a 95% alcohol at room temperature for 15 seconds to acclimate, and counterstaining was performed with a water-soluble eosin solution for 10 minutes.

Figure 3:
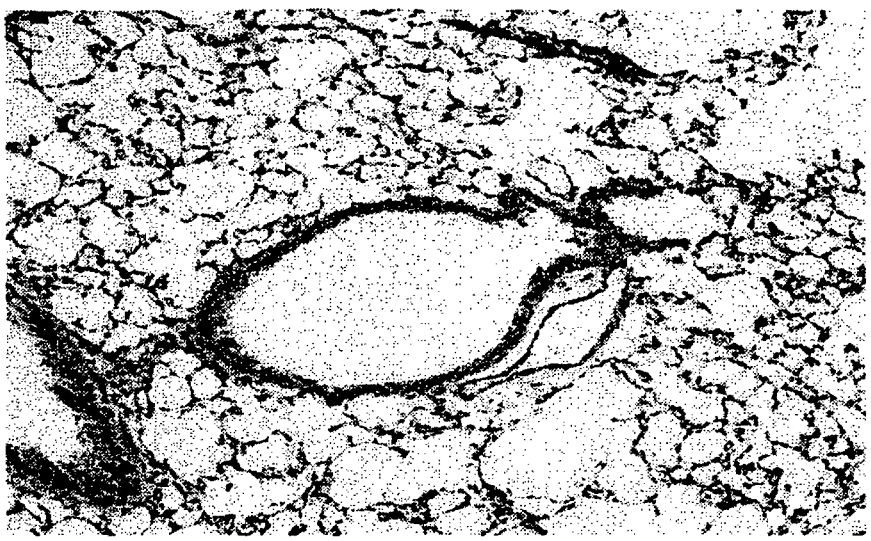
FIG. 3 is a view showing a tissue specimen photograph in which influence of HGF administration on increase in the number of invasion of inflammation cells in the tissue surrounding bronchi/vessels is histologically observed in a model mouse of bronchial asthma 48 hours after antigen inhalation exposure: (a) indicates a control group (non-sensitized/non-exposed), (b) indicates a physiological saline-administered group (sensitized/exposed+physiological saline), and (c) indicates an HGF-administered group (sensitized/exposed+HGF).
Figure 3:
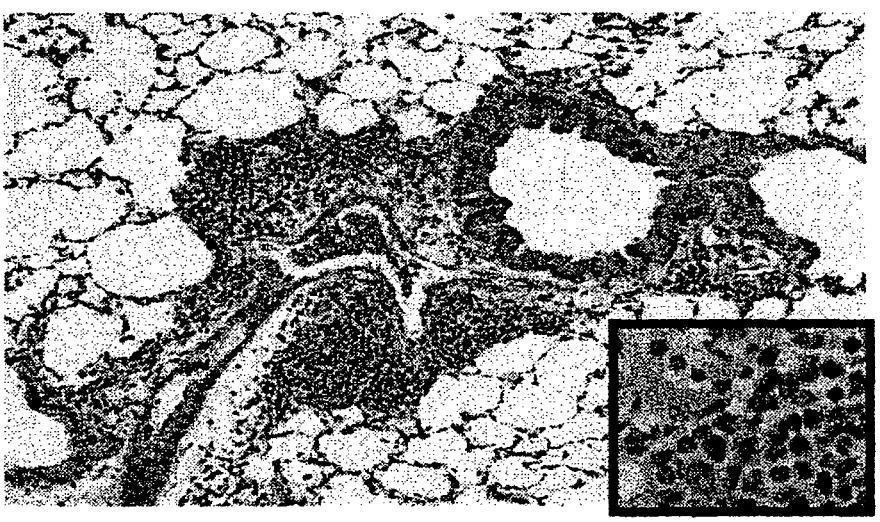
Figure 3:
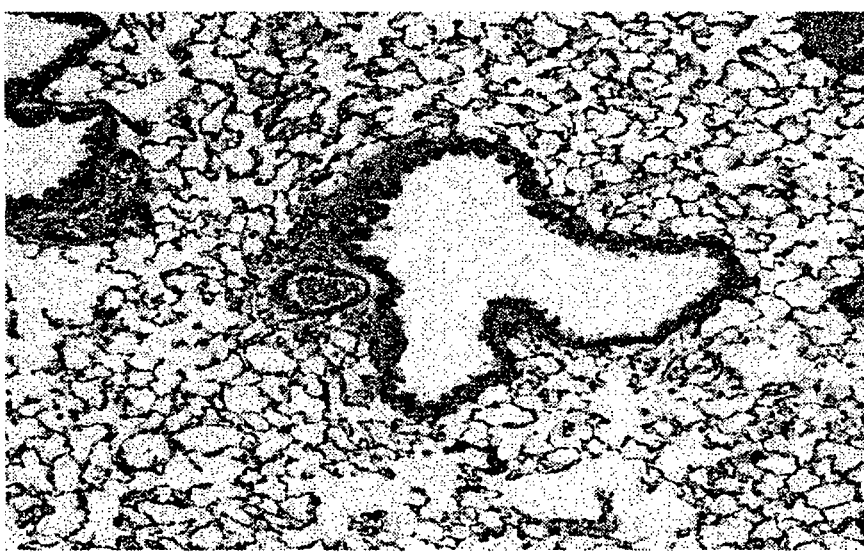
Figure 4:
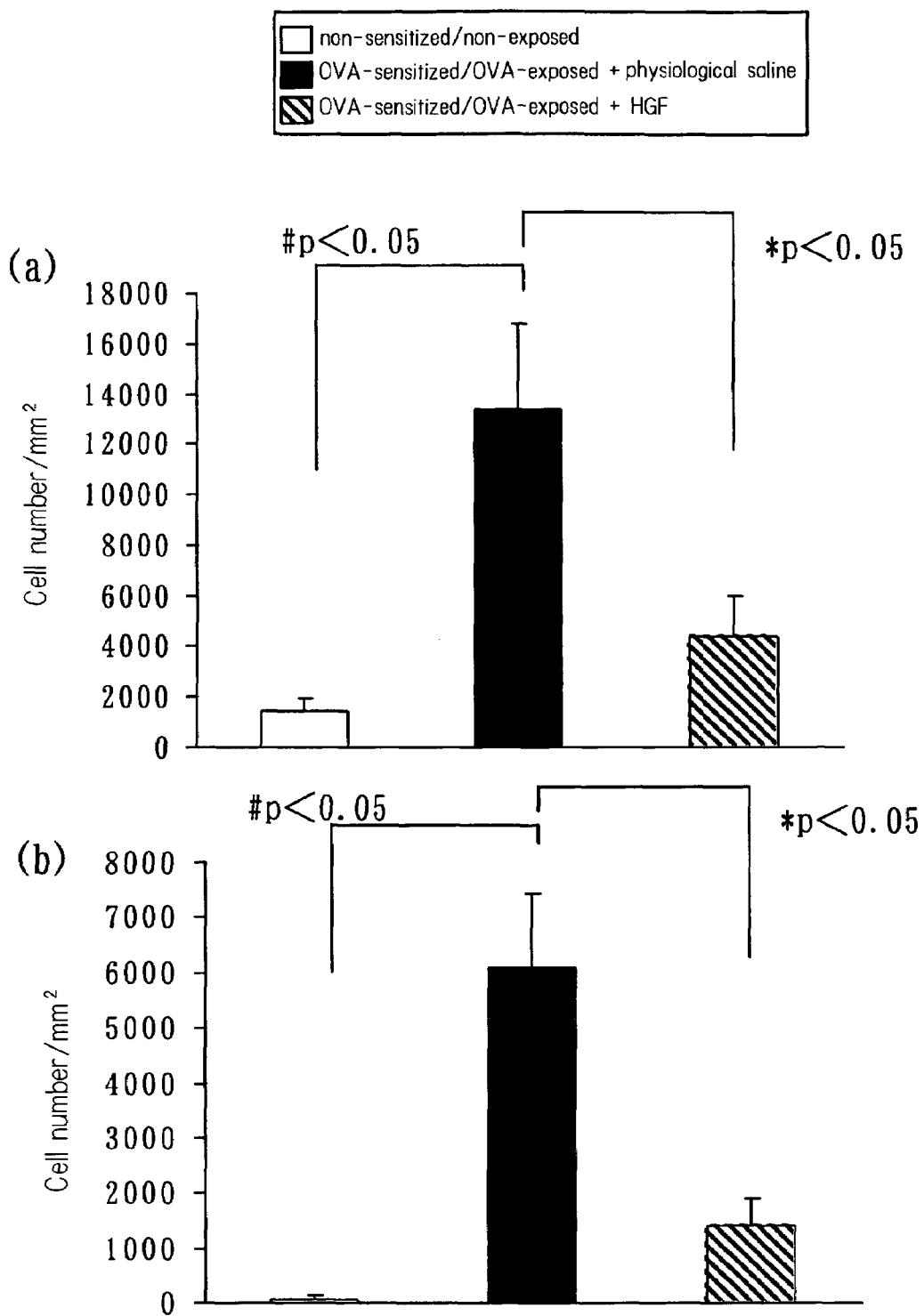
FIG. 4 is a view showing influence of HGF administration on increase in (a) the number of total inflammation cells of invasion and (b) the number of eosinophils in a tissue surrounding bronchia/vessels in a model mouse of bronchial asthma 48 hours after antigen inhalation exposure.

The results are shown in FIG. 3 and FIG. 4. Invasion of inflammation cells was scarcely seen in the tissue surrounding bronchi/vessels in the control group [FIG. 3-(a)], while invasion of inflammation cells was seen [FIG. 3-(b)], and the number of inflammation cells and the number of eosinophils were remarkably increased in a physiological saline-administered group (FIG. 4). To the contrary, in the HGF-administered group, an extent of invasion of inflammation cells was low as compared with a physiological saline-administered group, and increase in the number of inflammation cells and the number of eosinophils was suppressed (FIG. 3(c), FIG. 4).

(4) Measurement of Number of Mucus-producing Cells (Goblet Cell) in Airway Epithelial Tissue A lung tissue block surrounding main bronchi containing an airway epithelial tissue was excised from the right lung fixed tissue of (3), and a tissue specimen slide was prepared. The tissue specimen slide was periodic acid Schiff-stained, and the number of visualized goblet cells was counted under a microscope (final magnification×1,000). For counting, NIH Image Analysis system (National Institute of Health, Bethesda, Md.) was used. The counting was performed for randomly selected ten fields, and an average of the number of cells per unit length (1 mm) of an airway epithelial base membrane was calculated.

In addition, the mucus content in the cells was determined by a color strength (staining rate) which was colored by periodic acid Schiff staining, and mucus-producing cells were classified into two kinds of cells having a staining rate of 50% or more and cells having a staining rate of 50% or less.

The periodic acid Schiff staining was performed as follows. A tissue specimen slide was deparaffined, and the specimen was immersed in a 1% aqueous periodic acid solution at room temperature, and oxidized. After washed with running water, the specimen was stained with a Schiff reagent at room temperature for 10 minutes, sufficiently washed with running water again, and nucleus-stained with a hematoxylin solution for 1 minute.

Figure 5:
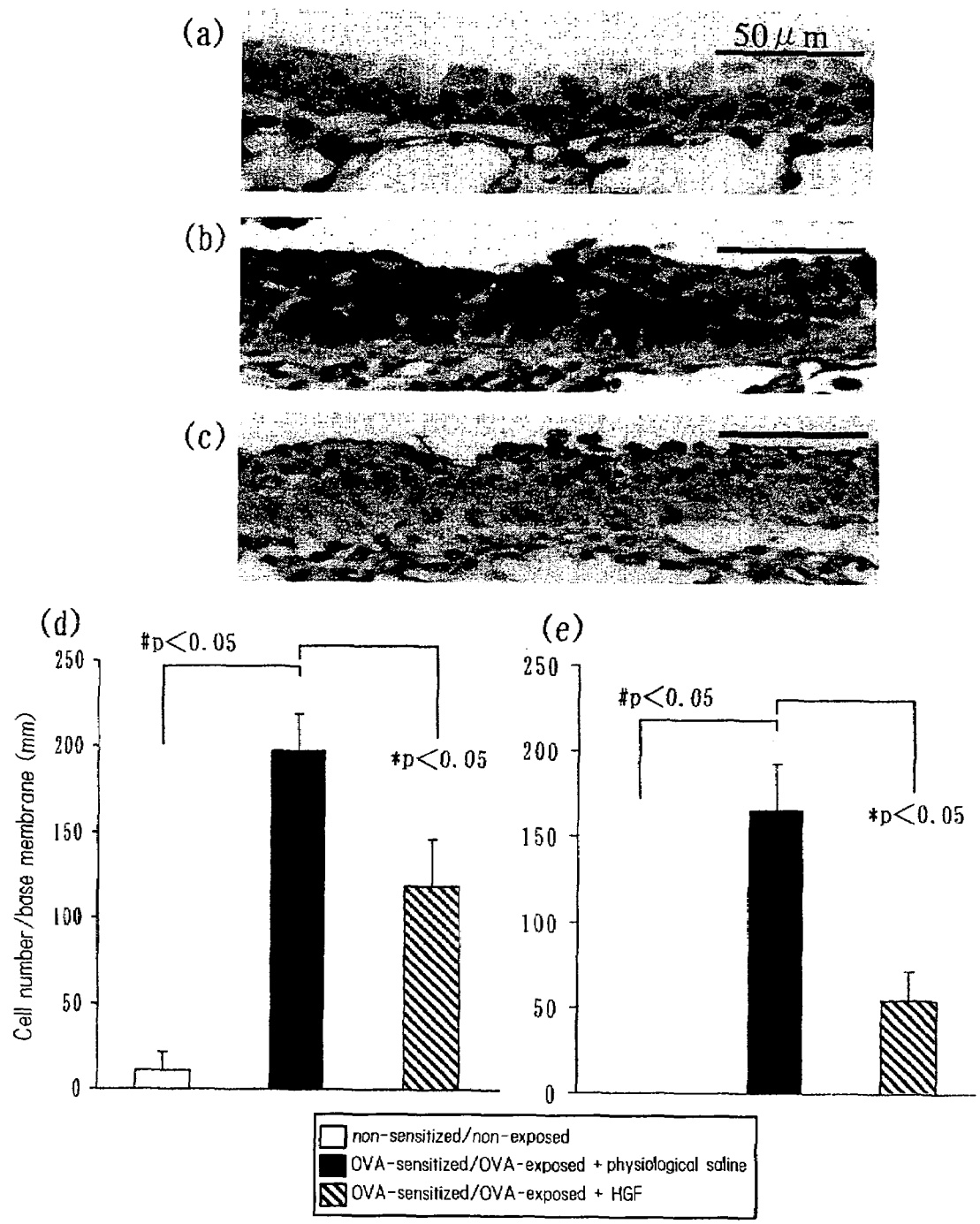
FIG. 5 is a view showing influence of HGF administration on increase in the number of mucus-producing cells (goblet cells) of the airway epithelium in a model mouse of bronchial asthma 48 hours after antigen inhalation exposure, wherein (a) is a view showing a tissue specimen photograph in which the airway epithelium of a control group (non-sensitized/non-exposed) is histologically observed, and (b) is a view showing a tissue specimen photograph in which the airway epithelium of a physiological saline-administered group (sensitized/exposed+physiological saline) is histologically observed, (c) is a view showing a tissue specimen photograph in which the airway epithelium of an HGF-administered group (sensitized/exposed+HGF) is histologically observed, (d) is a view showing the number of mucus-producing cells in the aforementioned respective groups, and (e) is a view showing the number of cells having a mucus content of 50% or more in the aforementioned respective groups.

The results are shown in FIG. 5. In the physiological saline-administered group [FIG. 5-(b)], the number of mucus-producing cells was remarkably increased [FIG. 5-(d)] compared to the control group [FIG. 5-(a)]. To the contrary, in the HGF-administered group, increase in the number of mucus-producing cells was suppressed [FIG. 5-(c), (d)], and moreover, the number of cells having a mucus content of 50% or more was remarkably low compared to the physiological saline-administered group (physiological saline-administered group: 165±27/mm, HGF-administered group: 54±16/mm), and it was confirmed that a secreted amount of mucus in each cell was reduced [FIG. 5-(e)].

(5) Measurement of Concentration of Cytokine and Growth Factor in BAL Fluid

A concentration of cytokines and growth factors in a BAL fluid was measured using a supernatant obtained by centrifugation (4° C., 3,000 rpm, 10 minutes) of a BAL fluid. IL-4, IL-5, IL-12, IL-13 and PDGF were measured using an ELISA kit of R&D (Minneapolis, Minn.), and TGF-β or NGF were measured using an ELISA kit of Promega (Madison, Wis.) or Chemicon (Temecula, Calif.) according to the method described in each attached instruction.

Figure 6:
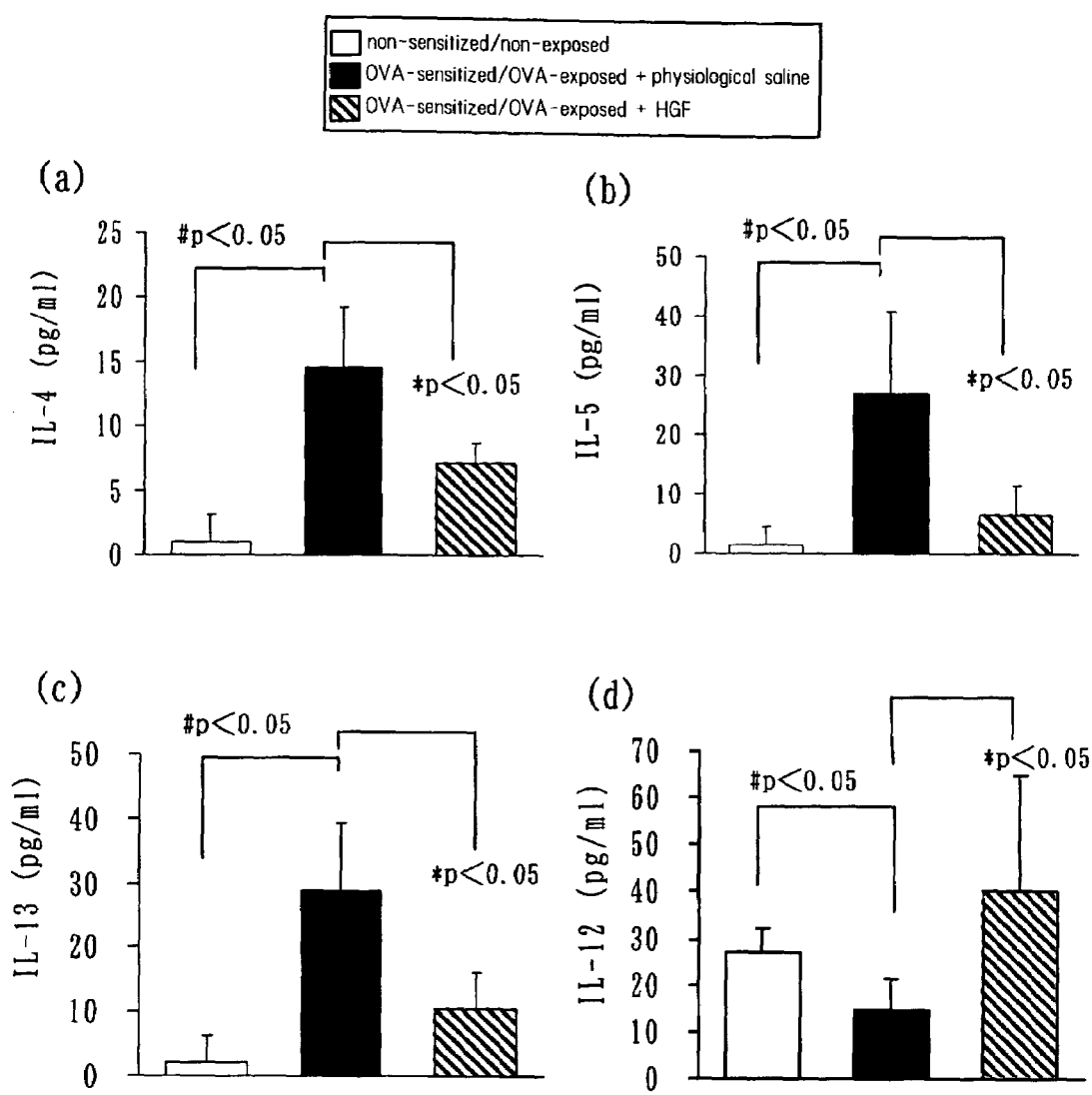
FIG. 6 is a view showing influence of HGF administration on a concentration of cytokines [(a) IL-4, (b) IL-5, (c) IL-13 and (d) IL-12] in a BAL fluid in a model mouse of bronchial asthma 48 hours after antigen inhalation exposure.
Figure 7:
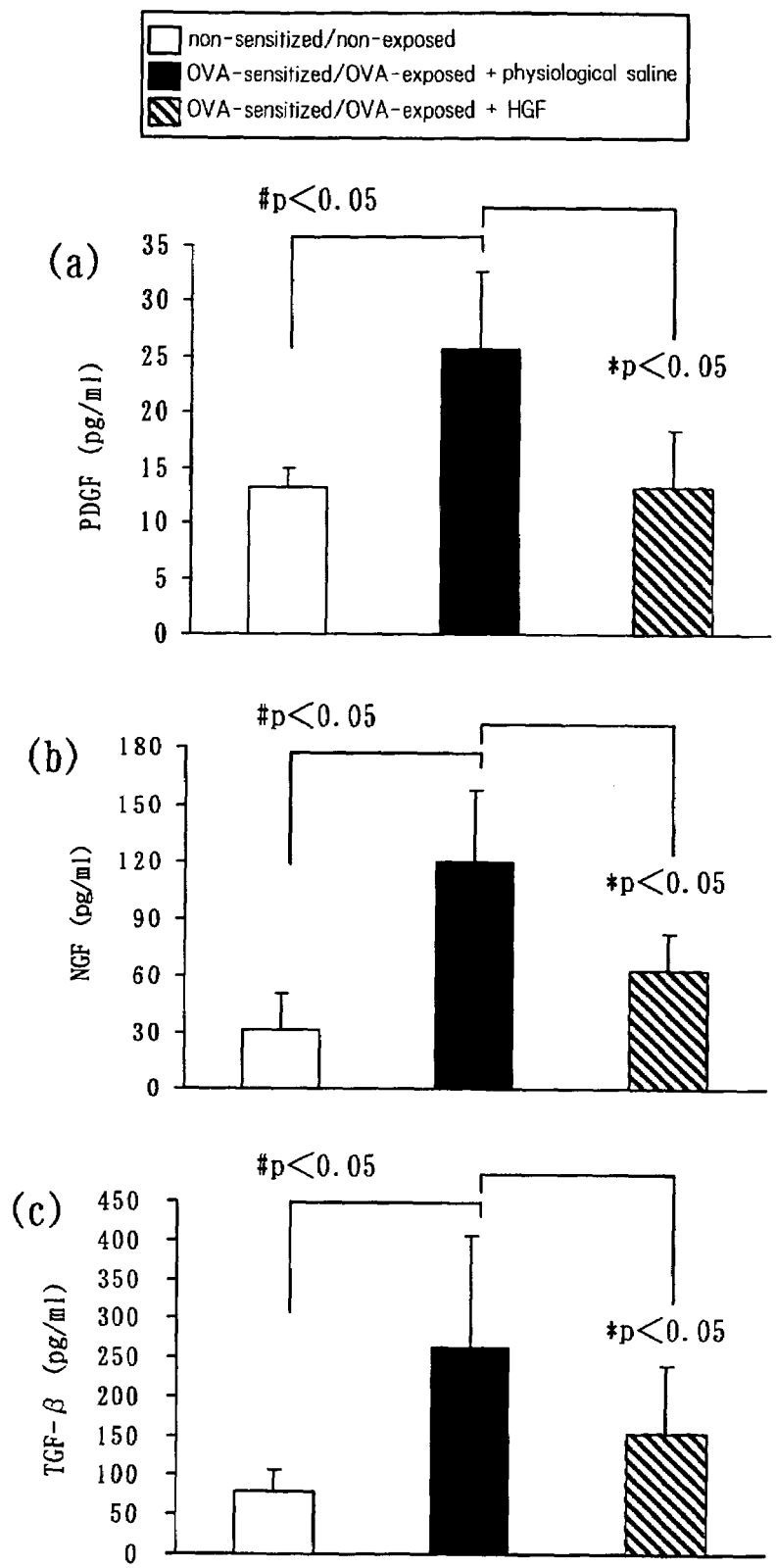
FIG. 7 is a view showing influence of HGF administration on increase in a concentration of growth factors [(a) PDGF, (b) NGF and (c) TGF-β] in a BAL fluid in a model mouse of bronchial asthma 48 hours after antigen inhalation exposure.

The results are shown in FIG. 6 and FIG. 7. In the physiological saline-administered group, each concentration of cytokines of IL-4, IL-5 and IL-13 [FIGS. 6-(a), (b) and (c)], and PDGF, NGF and TGF-β [FIGS. 7-(a), (b) and (c)] was remarkably increased compared to the control group. To the contrary, in the HGF-administered group, each concentration of them was significantly suppressed. On the other hand, an IL-12 concentration was decreased in the physiological saline-administered group, but significantly increased in the HGF-administered group compared to the control group [FIG. 6-(d)].

(6) Accumulation of TGF-β in Lung Tissue

The left lung after alveolus washing of (2) was dehydrated with 70% ethanol for 12 hours. The dehydrated left lung was fixed with paraffin, and a tissue specimen slide was prepared similarly to the procedure of (3). Anti-TGF-β rabbit IgG (Promega, Madison, Wis.) was adsorbed onto a tissue specimen (1:250), then this was immunostained with avidin-biotin, and TGF-β in the tissue was visualized, and observed under a microscope (final magnification×1,000).

Adsorption of anti-TGF-β rabbit IgG was performed at 4° C. for 12 hours, and avidin-biotin treatment was performed at room temperature for 60 minutes. A reaction of a peroxidase-labeled polymer reagent was performed at room temperature for 15 minutes under light shielding.

Figure 8:
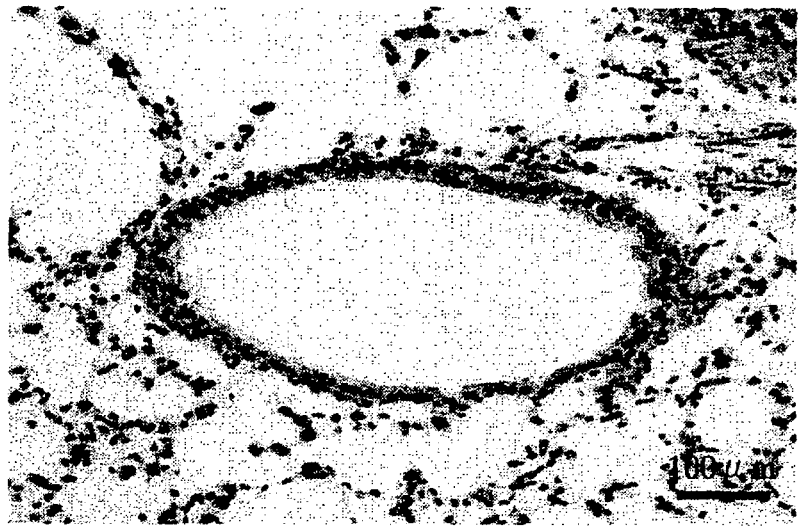
FIG. 8 is a view showing a tissue specimen photograph in which influence of HGF administration on accumulation of TGF-β in the lung tissue is histologically observed in a model mouse of bronchial asthma 48 hours after antigen inhalation exposure: (a) indicates a control group (non-sensitized/non-exposed), (b) indicates a physiological saline-administered group (sensitized/exposed+physiological saline), and (c) indicates an HGF-administered group (sensitized/exposed+HGF).
Figure 8:
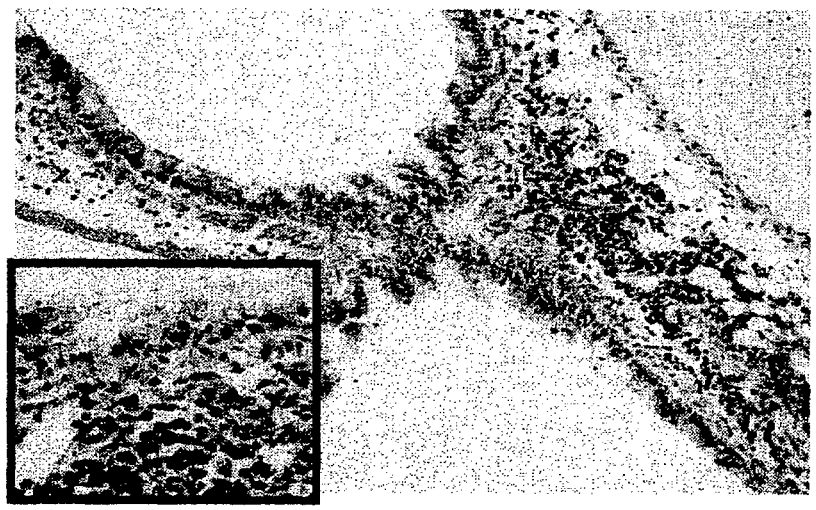
Figure 8:

As a result, in the physiological saline-administered group [FIG. 8-(b)], most of airway epithelium and inflammation cells were stained compared to the control group [FIG. 8-(a)], and it was confirmed that TGF-β was produced in the cells. To the contrary, in the HGF-administered group [FIG. 8-(c)], the number of stained cells was smaller compared to the physiological saline-administered group, and thus it was confirmed that production of TGF-β was suppressed.

(7) Measurement of Amount of Serum Antigen-specific IgE Antibody (Anti-OVA IgE)

A blood sample was collected from the inferior vena cava of mice in each group, and centrifuged at 4° C. and 1,500 rpm for 20 minutes to prepare a serum sample.

A PBS diluent containing 5 μg/mL monoclonal anti-mouse IgE antibody (Serotec) was dispensed on a 96-well plate (NUNC IMMUNOPLATE I: Nunc) at 100 μL/well, followed by a reaction overnight at 4° C. to coat a plate. Thereafter, each well was washed five times with 0.1% Tween 20-PBS (−) (not containing $Ca^{2+}$ and $Mg^{2+}$) (washing buffer), and 1% BSA (manufactured by Wako Pure Chemical Industries, Ltd.)-PBS was added at 150 μL/well, followed by incubation at room temperature for 1 hour. Then, this washed five times with a washing buffer, each 100 μL/well of a saline sample of mice in each group was added, and this was incubated at room temperature for 1 hour. At the same time, for producing a standard curve, a monoclonal anti-OVA-specific IgE antibody which had been quantitated in advance in a system for measuring a total amount of an IgE antibody was diluted to various concentrations with 1% BSA-0.1% Tween 20-PBS (diluting buffer), and this was added to another well of the same plate. After each well washed five times with a washing buffer, biotin-labeled OVA which had been 50-fold diluted with a diluting buffer was added at 100 μL/well, and this was incubated at room temperature for 1 hour. Each well washed five times with a washing buffer, peroxidase conjugated streptavidin DAKO which had been 3000-fold diluted with a diluting buffer was added at 100 μL/well and this was further incubated at room temperature for 1 hour. Each well washed five times with a washing buffer, a substrate solution (containing 0.1 M citric acid, 0.2 M $NaHPO_4$, o-phenylenediamine, and 30% $H_2O_2$) was added at 100 μL/well, this was reacted at room temperature for about 30 minutes in a dark place, and absorbance of each well of the plate was measured at 492 nm.

Figure 9:
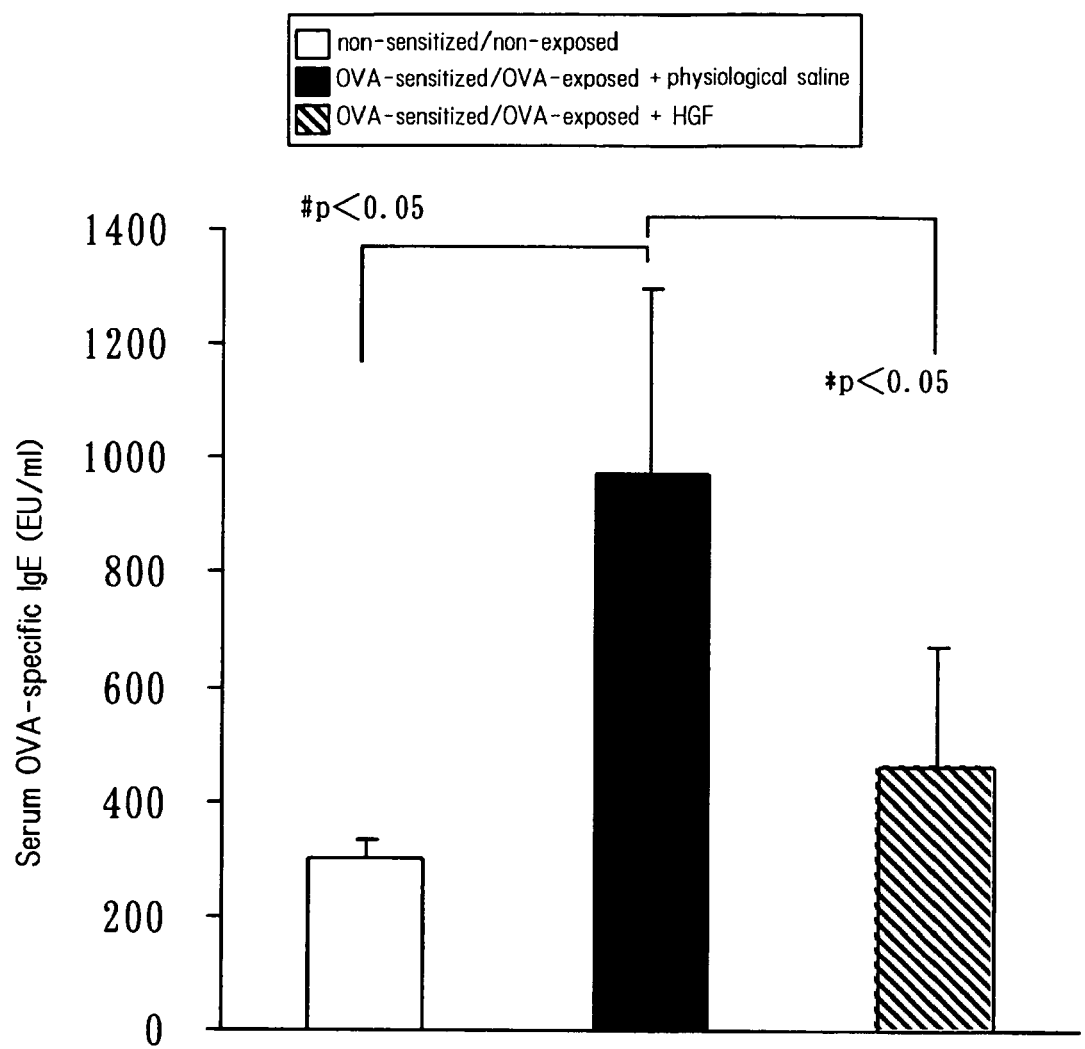
FIG. 9 is a view showing influence of HGF on increase in an amount of a serum antigen-specific IgE antibody (anti-OVA-specific IgE) in a model mouse of bronchial asthma 48 hours after antigen inhalation exposure.

The results are shown in FIG. 9. In the physiological saline-administered group, a concentration of anti-OVA-specific IgE was increased remarkably compared to the control group. To the contrary, in the HGF-administered group, increase in the concentration of anti-OVA-specific IgE was suppressed.

INDUSTRIAL APPLICABILITY

Since the preventive or therapeutic agent for asthma of the present invention suppresses the invasion of inflammation cells into the airway epithelium and subepithelium confirmed at the occurrence of airway inflammation, and also suppresses increase in the concentration of Th2 cytokines, growth factors and the like in the airway tissue, it can extremely effectively suppresses an inflammation reaction in bronchial asthma, and can prevent transference to chronic asthma or severe/refractory asthma. Moreover, since an active ingredient of the present agent is HGF derived from a living body, or a DNA encoding the HGF, there is no side effect which has been seen in previous steroid inhalation, when the agent is administered to a living body. Therefore, the preventive or therapeutic agent of asthma of the present invention is very safe and useful to a living body.

The present application is based on Japanese Patent Application No. 2003-086268 which was filed in Japan, and entire content thereof is incorporated by reference.

The invention claimed is:

1. A method for treating asthma comprising administering an effective amount of hepatocyte growth factor (HGF) or a physiologically acceptable salt thereof to a human, wherein the HGF comprises SEQ ID NO: 1 or SEQ ID NO: 2, and wherein the HGF is effective in suppressing airway inflammation.

2. The method according to claim 1, wherein the HGF comprises SEQ ID NO: 1.

3. The method according to claim 1, wherein the HGF comprises SEQ ID NO: 2.

4. The method according to claim 1, wherein the HGF is administered intravenously at a dose of about 250 to 1000 μg/Kg/day.

5. The method according to claim 1, wherein the HGF or a physiologically acceptable salt thereof and physiologically acceptable carrier are administered.

6. The method for suppressing an inflammation reaction in bronchial asthma comprising administering an effective amount of hepatocyte growth factor (HGF) or a physiologically acceptable salt thereof to a human, wherein the HGF comprises SEQ ID NO: 1 or SEQ ID NO: 2, and wherein the HGF is effective in suppressing the inflammation reaction in bronchial asthma.

7. The method according to claim 6, wherein the HGF comprises SEQ ID NO: 1.

8. The method according to claim 6, wherein the HGF comprises SEQ ID NO: 2.

9. The method according to claim 6, wherein the HGF is administered intravenously at a dose of about 250 to 1000 μg/Kg/day.

10. The method according to claim 6, wherein the HGF or a physiologically acceptable salt therof and a physiologically acceptable carrier are administered.

* * * * *

SEQUENCE LISTING

```
<160> NUMBER OF SEQ ID NOS: 6

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125
```

```
Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
            165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
```

```
                545                 550                 555                 560
            Cys Lys Gln Val Leu Asn Val Ser Gln Leu Val Tyr Gly Pro Glu Gly
                            565                 570                 575

Ser Asp Leu Val Leu Met Lys Leu Ala Arg Pro Ala Val Leu Asp Asp
                        580                 585                 590

Phe Val Ser Thr Ile Asp Leu Pro Asn Tyr Gly Cys Thr Ile Pro Glu
                        595                 600                 605

Lys Thr Ser Cys Ser Val Tyr Gly Trp Gly Tyr Thr Gly Leu Ile Asn
                        610                 615                 620

Tyr Asp Gly Leu Leu Arg Val Ala His Leu Tyr Ile Met Gly Asn Glu
            625                 630                 635                 640

Lys Cys Ser Gln His His Arg Gly Lys Val Thr Leu Asn Glu Ser Glu
                            645                 650                 655

Ile Cys Ala Gly Ala Glu Lys Ile Gly Ser Gly Pro Cys Glu Gly Asp
                            660                 665                 670

Tyr Gly Gly Pro Leu Val Cys Glu Gln His Lys Met Arg Met Val Leu
                        675                 680                 685

Gly Val Ile Val Pro Gly Arg Gly Cys Ala Ile Pro Asn Arg Pro Gly
                        690                 695                 700

Ile Phe Val Arg Val Ala Tyr Tyr Ala Lys Trp Ile His Lys Ile Ile
            705                 710                 715                 720

Leu Thr Tyr Lys Val Pro Gln Ser
                        725

<210> SEQ ID NO 2
<211> LENGTH: 723
<212> TYPE: PRT
<213> ORGANISM: Homo sapiens

<400> SEQUENCE: 2

Met Trp Val Thr Lys Leu Leu Pro Ala Leu Leu Leu Gln His Val Leu
            1               5                   10                  15

Leu His Leu Leu Leu Leu Pro Ile Ala Ile Pro Tyr Ala Glu Gly Gln
                        20                  25                  30

Arg Lys Arg Arg Asn Thr Ile His Glu Phe Lys Lys Ser Ala Lys Thr
                    35                  40                  45

Thr Leu Ile Lys Ile Asp Pro Ala Leu Lys Ile Lys Thr Lys Lys Val
                50                  55                  60

Asn Thr Ala Asp Gln Cys Ala Asn Arg Cys Thr Arg Asn Lys Gly Leu
            65                  70                  75                  80

Pro Phe Thr Cys Lys Ala Phe Val Phe Asp Lys Ala Arg Lys Gln Cys
                            85                  90                  95

Leu Trp Phe Pro Phe Asn Ser Met Ser Ser Gly Val Lys Lys Glu Phe
                        100                 105                 110

Gly His Glu Phe Asp Leu Tyr Glu Asn Lys Asp Tyr Ile Arg Asn Cys
                    115                 120                 125

Ile Ile Gly Lys Gly Arg Ser Tyr Lys Gly Thr Val Ser Ile Thr Lys
                130                 135                 140

Ser Gly Ile Lys Cys Gln Pro Trp Ser Ser Met Ile Pro His Glu His
            145                 150                 155                 160

Ser Tyr Arg Gly Lys Asp Leu Gln Glu Asn Tyr Cys Arg Asn Pro Arg
                            165                 170                 175

Gly Glu Glu Gly Gly Pro Trp Cys Phe Thr Ser Asn Pro Glu Val Arg
                        180                 185                 190
```

```
Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
        210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
        260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
        290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
        340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
        370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
        420                 425                 430

Asn Tyr Cys Arg Asn Pro Asp Asp Ala His Gly Pro Trp Cys Tyr
        435                 440                 445

Thr Gly Asn Pro Leu Ile Pro Trp Asp Tyr Cys Pro Ile Ser Arg Cys
        450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
        500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
        530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
        580                 585                 590

Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Leu Leu
```

```
           610                 615                 620
Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
                660                 665                 670

Val Cys Glu Gln His Lys Met Arg Met Val Leu Gly Val Ile Val Pro
            675                 680                 685

Gly Arg Gly Cys Ala Ile Pro Asn Arg Pro Gly Ile Phe Val Arg Val
        690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 3
<211> LENGTH: 2187
<212> TYPE: DNA
<213> ORGANISM: Homo sapiens

<400> SEQUENCE: 3
```

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa atcagcaaa gactaccta atcaaaatag atccagcact gaagataaaa | 180 |
| accaaaaaag tgaatactgc agaccaatgt gctaatagat gtactaggaa taaggactt | 240 |
| ccattcactt gcaaggcttt tgttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| agcttttgc cttcgagcta tcggggtaaa gacctacagg aaaactactg tcgaaatcct | 540 |
| cgaggggaag aaggggggacc ctggtgtttc acaagcaatc cagaggtacg ctacgaagtc | 600 |
| tgtgacattc ctcagtgttc agaagttgaa tgcatgacct gcaatgggga gagttatcga | 660 |
| ggtctcatgg atcatacaga atcaggcaag atttgtcagc gctgggatca tcagacacca | 720 |
| caccggcaca aattcttgcc tgaaagatat cccgacaagg gctttgatga taattattgc | 780 |
| cgcaatcccg atggccagcc gaggccatgg tgctatactc ttgaccctca cacccgctgg | 840 |
| gagtactgtg caattaaaac atgcgctgac aatactatga tgacactga tgttcctttg | 900 |
| gaaacaactg aatgcatcca aggtcaagga gaaggctaca gggcactgt caataccatt | 960 |
| tggaatggaa ttccatgtca gcgttgggat tctcagtatc ctcacgagca tgacatgact | 1020 |
| cctgaaaatt tcaagtgcaa ggacctacga gaaaattact gccgaaatcc agatgggtct | 1080 |
| gaatcaccct ggtgttttac cactgatcca aacatccgag ttggctactg ctcccaaatt | 1140 |
| ccaaactgtg atatgtcaca tggacaagat tgttatcgtg gaatggcaa aaattatatg | 1200 |
| ggcaacttat cccaaacaag atctggacta acatgttcaa tgtgggacaa gaacatggaa | 1260 |
| gacttacatc gtcatatctt ctgggaacca gatgcaagta agctgaatga gaattactgc | 1320 |
| cgaaatccag atgatgatgc tcatggaccc tggtgctaca cgggaaatcc actcattcct | 1380 |
| tgggattatt gccctatttc tcgttgtgaa ggtgatacca cacctacaat agtcaattta | 1440 |
| gaccatccg taatatcttg tgccaaaacg aaacaattgc gagttgtaaa tgggattcca | 1500 |

| | |
|---|---|
| acacgaacaa acataggatg gatggttagt ttgagataca gaaataaaca tatctgcgga | 1560 |
| ggatcattga taaaggagag ttgggttctt actgcacgac agtgtttccc ttctcgagac | 1620 |
| ttgaaagatt atgaagcttg gcttggaatt catgatgtcc acggaagagg agatgagaaa | 1680 |
| tgcaaacagg ttctcaatgt tcccagctg gtatatggcc ctgaaggatc agatctggtt | 1740 |
| ttaatgaagc ttgccaggcc tgctgtcctg atgattttg ttagtacgat tgatttacct | 1800 |
| aattatggat gcacaattcc tgaaaagacc agttgcagtg tttatggctg ggctacact | 1860 |
| ggattgatca actatgatgg cctattacga gtggcacatc tctatataat gggaaatgag | 1920 |
| aaatgcagcc agcatcatcg agggaaggtg actctgaatg agtctgaaat atgtgctggg | 1980 |
| gctgaaaaga ttggatcagg accatgtgag ggggattatg gtggcccact tgtttgtgag | 2040 |
| caacataaaa tgagaatggt tcttggtgtc attgttcctg gtcgtggatg tgccattcca | 2100 |
| aatcgtcctg gtattttgt ccgagtagca tattatgcaa aatggataca caaaattatt | 2160 |
| ttaacatata aggtaccaca gtcatag | 2187 |

```
<210> SEQ ID NO 4
<211> LENGTH: 2172
<212> TYPE: DNA
<213> ORGANISM: Homo sapiens

<400> SEQUENCE: 4
```

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aaagaagaaa tacaattcat | 120 |
| gaattcaaaa atcagcaaa gactacccta atcaaaatag atccagcact gaagataaaa | 180 |
| accaaaaaag tgaatactgc agaccaatgt gctaatagat gtactaggaa taaggactt | 240 |
| ccattcactt gcaaggcttt tgttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| agctatcggg gtaaagacct acaggaaaac tactgtcgaa atcctcgagg ggaagaaggg | 540 |
| ggaccctggt gttcacaag caatccgag gtacgctacg aagtctgtga cattcctcag | 600 |
| tgttcagaag ttgaatgcat gacctgcaat ggggagagtt atcgaggtct catggatcat | 660 |
| acagaatcag gcaagatttg tcagcgctgg atcatcaga caccacaccg gcacaaattc | 720 |
| ttgcctgaaa gatatcccga caagggctt gatgataatt attgccgcaa tcccgatggc | 780 |
| cagccgaggc catggtgcta tactcttgac cctcacaccc gctgggagta ctgtgcaatt | 840 |
| aaaacatgcg ctgacaatac tatgaatgac actgatgttc ctttggaaac aactgaatgc | 900 |
| atccaaggtc aaggagaagg ctacaggggc actgtcaata ccatttggaa tggaattcca | 960 |
| tgtcagcgtt gggattctca gtatcctcac gagcatgaca tgactcctga aaatttcaag | 1020 |
| tgcaaggacc tacgagaaaa ttactgccga aatccagatg gtctgaatc accctggtgt | 1080 |
| tttaccactg atccaaacat ccgagttggc tactgctccc aaattccaaa ctgtgatatg | 1140 |
| tcacatggac aagattgtta tcgtgggaat ggcaaaaatt atatgggcaa cttatcccaa | 1200 |
| acaagatctg gactaacatg ttcaatgtgg gacaagaaca tggaagactt acatcgtcat | 1260 |
| atcttctggg aaccagatgc aagtaagctg aatgagaatt actgccgaaa tccagatgat | 1320 |
| gatgctcatg gaccctggtg ctacacggga aatccactca ttccttggga ttattgccct | 1380 |

```
atttctcgtt gtgaaggtga taccacacct acaatagtca atttagacca tcccgtaata    1440
tcttgtgcca aaacgaaaca attgcgagtt gtaaatggga ttccaacacg aacaaacata    1500
ggatggatgg ttagtttgag atacagaaat aaacatatct gcggaggatc attgataaag    1560
gagagttggg ttcttactgc acgacagtgt ttcccttctc gagacttgaa agattatgaa    1620
gcttggcttg gaattcatga tgtccacgga agaggagatg agaaatgcaa acaggttctc    1680
aatgtttccc agctggtata tggccctgaa ggatcagatc tggttttaat gaagcttgcc    1740
aggcctgctg tcctggatga ttttgttagt acgattgatt tacctaatta tggatgcaca    1800
attcctgaaa agaccagttg cagtgtttat ggctggggct acactggatt gatcaactat    1860
gatggcctat tacgagtggc acatctctat ataatgggaa atgagaaatg cagccagcat    1920
catcgaggga aggtgactct gaatgagtct gaaatatgtg ctggggctga aaagattgga    1980
tcaggaccat gtgagggga ttatggtggc ccacttgttt gtgagcaaca taaaatgaga    2040
atggttcttg gtgtcattgt tcctggtcgt ggatgtgcca ttccaaatcg tcctggtatt    2100
tttgtccgag tagcatatta tgcaaaatgg atacacaaaa ttattttaac atataaggta    2160
ccacagtcat ag                                                        2172

<210> SEQ ID NO 5
<211> LENGTH: 28
<212> TYPE: DNA
<213> ORGANISM: Artificial
<220> FEATURE:
<223> OTHER INFORMATION: synthetic construct

<400> SEQUENCE: 5
cccgtccagc ggtaccatgt gggtgacc                                       28

<210> SEQ ID NO 6
<211> LENGTH: 29
<212> TYPE: DNA
<213> ORGANISM: Artificial
<220> FEATURE:
<223> OTHER INFORMATION: synthetic construct

<400> SEQUENCE: 6
tacgggatgg actagttaga ctattgtag                                      29
```